US009325148B2

(12) United States Patent
Karavitis

(10) Patent No.: US 9,325,148 B2
(45) Date of Patent: *Apr. 26, 2016

(54) HIGH POWER FEMTOSECOND LASER WITH VARIABLE REPETITION RATE

(71) Applicant: Alcon LenSx, Inc., Aliso Viejo, CA (US)

(72) Inventor: Michael Karavitis, San Pedro, CA (US)

(73) Assignee: Alcon LenSx, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/581,623

(22) Filed: Dec. 23, 2014

(65) Prior Publication Data

US 2015/0117480 A1    Apr. 30, 2015

Related U.S. Application Data

(63) Continuation of application No. 12/712,067, filed on Feb. 24, 2010, now Pat. No. 8,953,651.

(51) Int. Cl.
*H01S 3/10* (2006.01)
*A61F 9/008* (2006.01)
(Continued)

(52) U.S. Cl.
CPC .......... *H01S 3/10046* (2013.01); *A61F 9/00825* (2013.01); *H01S 3/0057* (2013.01); *A61F 2009/00897* (2013.01); *H01S 3/235* (2013.01)

(58) Field of Classification Search
CPC .... H01S 3/0057; H01S 3/10046; H01S 3/235
See application file for complete search history.

(56) References Cited

U.S. PATENT DOCUMENTS

| 4,896,119 A | 1/1990 | Williamson et al. |
| 5,221,988 A | 6/1993 | Juhasz |
| 5,329,398 A | 7/1994 | Lai et al. |

(Continued)

FOREIGN PATENT DOCUMENTS

| WO | WO 2004068651 A2 * | 8/2004 | ............... H01S 3/00 |
| WO | WO 2009098459 A1 | 8/2009 | ............. H01L 31/29 |

OTHER PUBLICATIONS

Rimington et al., "Femtosecond Ti:Sapphire Oscillator Electro-Optically Cavity Dumped at 50kHz," Sep. 20, 2001, Applied Optics, vol. 40, No. 27, 4831-4835.

(Continued)

*Primary Examiner* — Joshua King
(74) *Attorney, Agent, or Firm* — S. Brannon Latimer

(57) ABSTRACT

Designs and techniques for constructing and operating femtosecond pulse lasers are provided. One example of a laser engine includes an oscillator that generates and outputs a beam of femtosecond seed pulses, a stretcher-compressor that stretches a duration of the seed pulses, and an amplifier that receives the stretched seed pulses, amplifies an amplitude of selected stretched seed pulses to create amplified stretched pulses, and outputs a laser beam of amplified stretched pulses back to the stretcher-compressor that compresses their duration and outputs a laser beam of femtosecond pulses. The amplifier includes a dispersion controller that compensates a dispersion of the amplified stretched pulses, making the repetition rate of the laser adjustable between procedures or according to the speed of scanning. The laser engine can be compact with a total optical path of less than 500 meters, and have a low number of optical elements, e.g. less than 50.

10 Claims, 12 Drawing Sheets

(51) Int. Cl.
*H01S 3/00* (2006.01)
*H01S 3/23* (2006.01)

(56) References Cited

U.S. PATENT DOCUMENTS

| | | | |
|---|---|---|---|
| 5,499,134 A * | 3/1996 | Galvanauskas et al. | 359/333 |
| 5,541,951 A | 7/1996 | Juhasz et al. | |
| 5,548,234 A | 8/1996 | Turi et al. | |
| 5,561,678 A | 10/1996 | Juhasz et al. | |
| 5,594,256 A | 1/1997 | Siebert | |
| 5,656,186 A | 8/1997 | Mourou et al. | |
| 5,701,319 A | 12/1997 | Fermann | |
| 5,730,811 A * | 3/1998 | Azad et al. | 148/565 |
| 5,734,503 A | 3/1998 | Szipocs et al. | |
| 5,847,863 A | 12/1998 | Galvanauskas et al. | |
| 5,867,304 A | 2/1999 | Galvanauskas et al. | |
| 6,081,543 A | 6/2000 | Liu et al. | 372/102 |
| 6,099,522 A | 8/2000 | Knopp et al. | |
| 6,174,648 B1 * | 1/2001 | Terao et al. | 430/321 |
| 6,198,568 B1 | 3/2001 | Galvanauskas et al. | |
| 6,208,458 B1 | 3/2001 | Galvanauskas et al. | |
| 6,231,566 B1 * | 5/2001 | Lai | 606/5 |
| 6,324,191 B1 | 11/2001 | Horvath | |
| 6,393,035 B1 | 5/2002 | Weingarten et al. | |
| 6,580,732 B1 | 6/2003 | Guch et al. | |
| 6,693,927 B1 | 2/2004 | Horvath et al. | |
| 6,726,679 B1 | 4/2004 | Dick et al. | |
| 6,785,303 B1 | 8/2004 | Holzwarth et al. | |
| 6,807,198 B1 | 10/2004 | Fürbach et al. | |
| 7,103,077 B2 | 9/2006 | Schuhmacher et al. | |
| 7,116,688 B2 | 10/2006 | Sauter et al. | |
| 7,131,968 B2 | 11/2006 | Bendett et al. | |
| 7,386,211 B1 | 6/2008 | Di Teodoro et al. | |
| 7,522,642 B2 | 4/2009 | Zadoyan et al. | |
| 7,643,521 B2 | 1/2010 | Loesel | |
| 8,953,651 B2 * | 2/2015 | Karavitis | 372/24 |
| 2003/0189756 A1 | 10/2003 | Erbert et al. | |
| 2003/0193975 A1 | 10/2003 | Pang | |
| 2004/0083814 A1 | 5/2004 | Lehmann et al. | 73/588 |
| 2004/0243111 A1 * | 12/2004 | Bendett et al. | 606/5 |
| 2004/0243112 A1 | 12/2004 | Bendett et al. | |
| 2005/0041702 A1 | 2/2005 | Martin et al. | |
| 2005/0079645 A1 | 4/2005 | Moriwaka | 438/29 |
| 2005/0111500 A1 | 5/2005 | Harter et al. | |
| 2005/0157382 A1 | 7/2005 | Kafka et al. | |
| 2005/0286599 A1 | 12/2005 | Rafac et al. | |
| 2006/0221449 A1 | 10/2006 | Glebov et al. | |
| 2007/0013995 A1 | 1/2007 | Kaertner et al. | |
| 2007/0041083 A1 | 2/2007 | De Teodoro et al. | |
| 2007/0091977 A1 | 4/2007 | Sohn et al. | |
| 2007/0098025 A1 * | 5/2007 | Hong et al. | 372/13 |
| 2008/0130099 A1 | 6/2008 | Harter | |
| 2008/0232407 A1 | 9/2008 | Harter et al. | |
| 2009/0086773 A1 | 4/2009 | Murison et al. | |
| 2009/0257464 A1 | 10/2009 | Dantus et al. | |
| 2011/0038390 A1 | 2/2011 | Rudd et al. | |
| 2011/0063597 A1 | 3/2011 | Mengel | |

OTHER PUBLICATIONS

European extended search report for corresponding EP application No. 11748058.2, with mailing date Oct. 2, 2013, 11 pages.

Fast Pulse Technology et al., Lasermetrics Division, "Model 5055SC Integrated Driver / Pockels Cell Q-Switching System", Internet Citation, 2008, 2 pages.

Huang et al., "Human dermis separation via ultra-short pulsed laser plasma-mediated ablation", Journal of Physics D. Applied Physics, 2009, vol. 42, No. 15, 1-9.

Juhasz, T. et al., "Corneal Refractive Surgery with Femtosecond Lasers", IEEE Journal of Selected Toics in Quantum Electornics, 1999, vol. 5, No. 4, 902-910.

Wynne et al., "Regenerative amplification of 30-fs pulses in Ti:sapphire at 5 kHz", 1994, Optics Letters, vol. 19, No. 12, 895-897.

Galvanauskas, et al.; "Use of Volume Chirped Bragg Gratings for Compact High-Energy Chirped Pulse Amplification Circuits"; CLEO; p. 362 (1998).

Cho, Cheon Whan, Authorized Officer, Korean Intellectual Property Office, PCT International Application No. PCT/ US2011/026061, in International Search Report, mailed Nov. 14, 2011, 10 pages.

Cho, Sung Chan, Authorized Officer, Korean Intellectual Property Office, PCT International Application No. PCT/ US2011/026055, in International Search Report, mailed Jan. 2, 2012, 9 pages.

Na, Sun Hee, Authorized Officer, Korean Intellectual Property Office, PCT International Application No. PCT/ US2011/026037, in International Search Report, mailed Oct. 26, 2011, 9 pages.

Cho, Cheon Whan, Authorized Officer, Korean Intellectual Property Office, PCT International Application No. PCT/ US2011/026031, in International Search Report, mailed Oct. 31, 2011, 9 pages.

Vicario et al., "Preliminary Results Using An Acousto-Optic Dispersive Filter For Laser Pulse Shaping", SPARC-LS-04/011, Jan. 15, 2004, 7 pages.

* cited by examiner

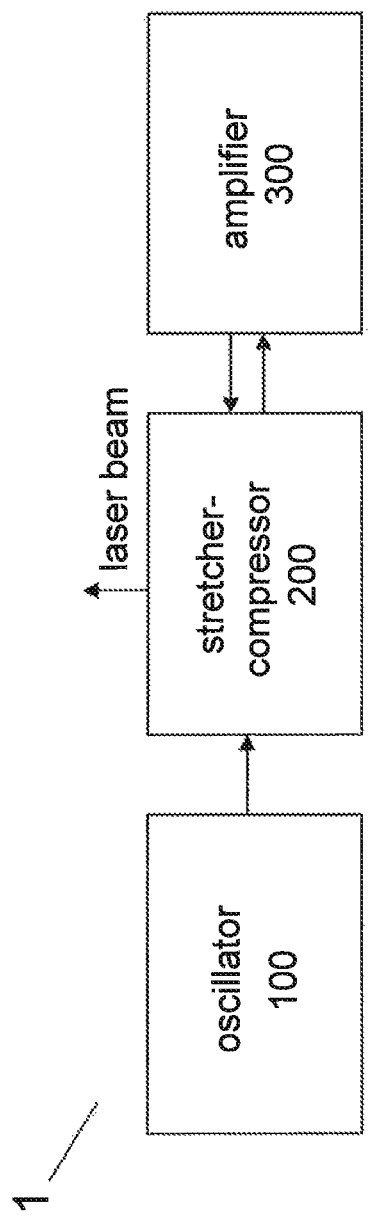
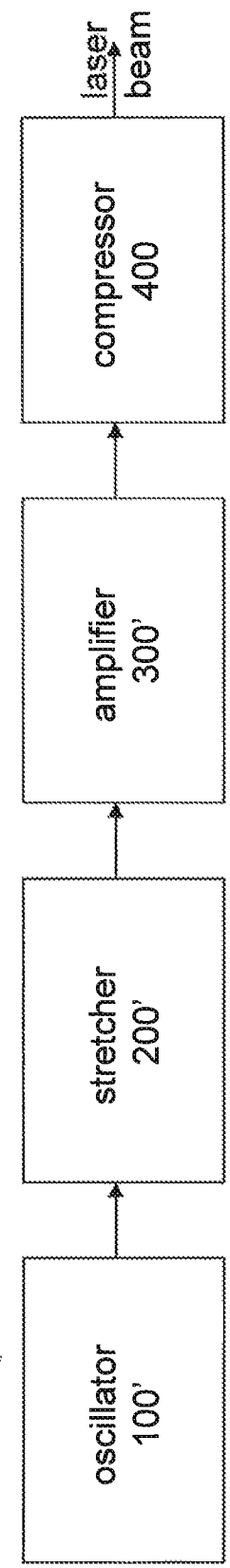
FIG. 1A
FIG. 1B

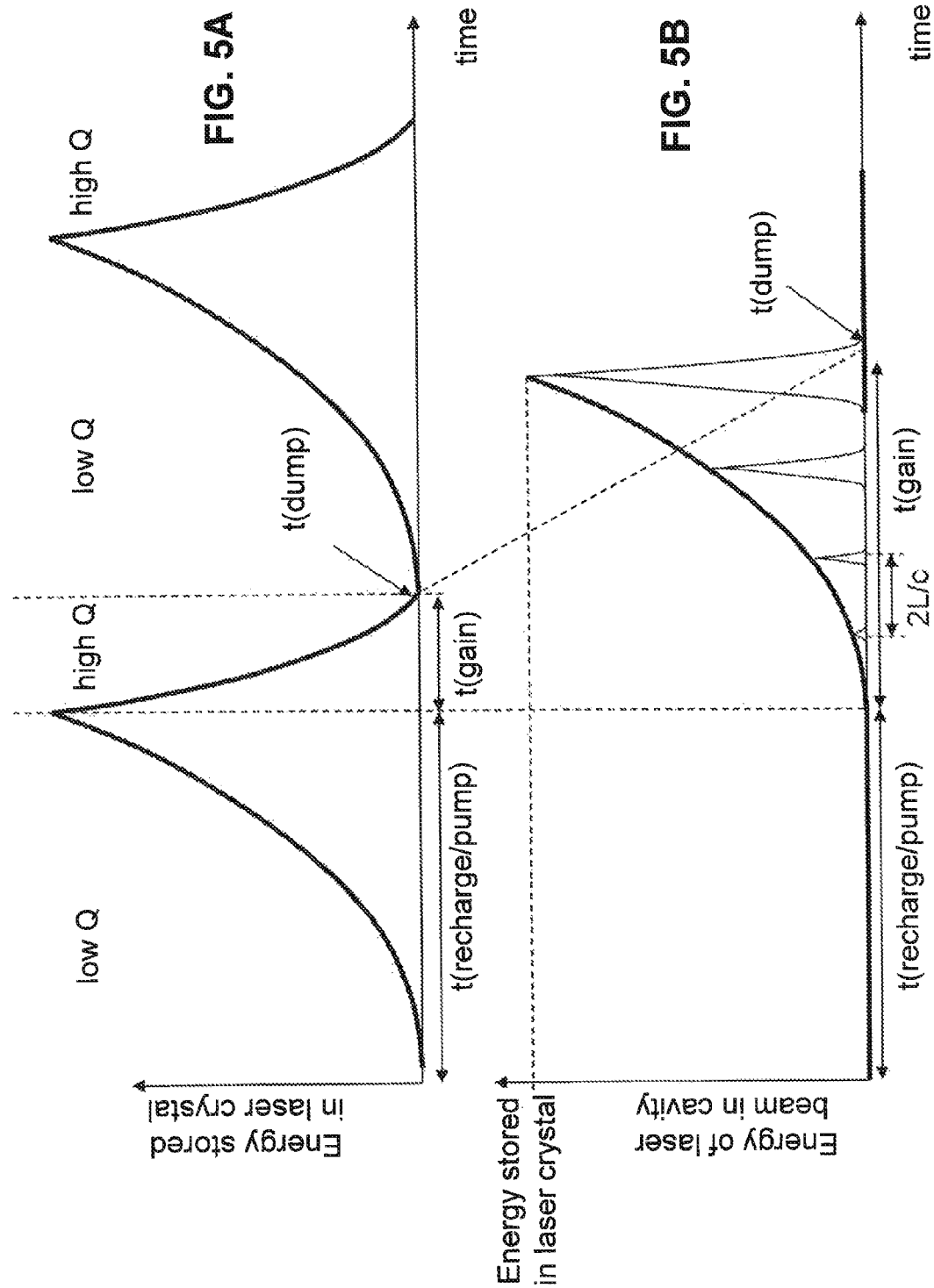

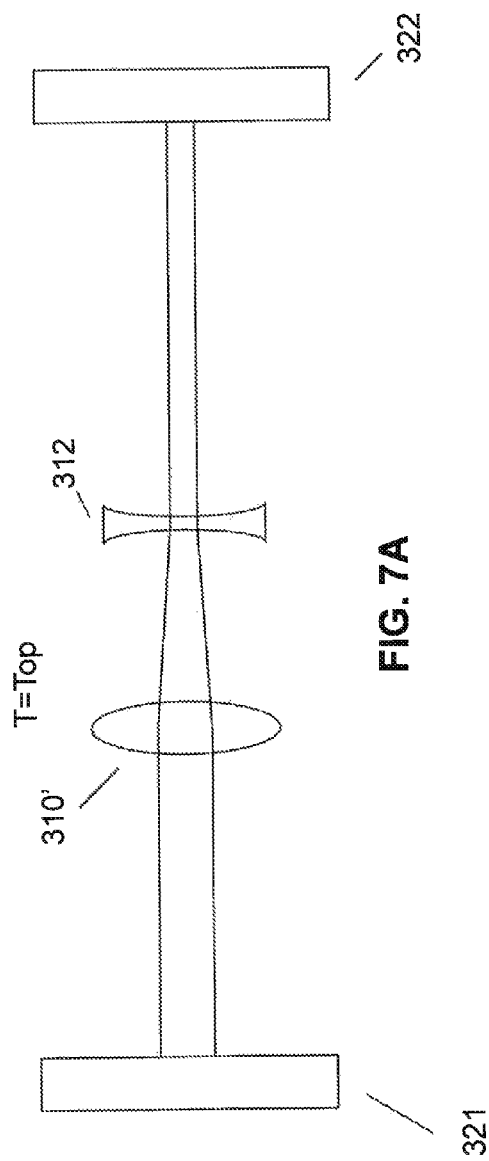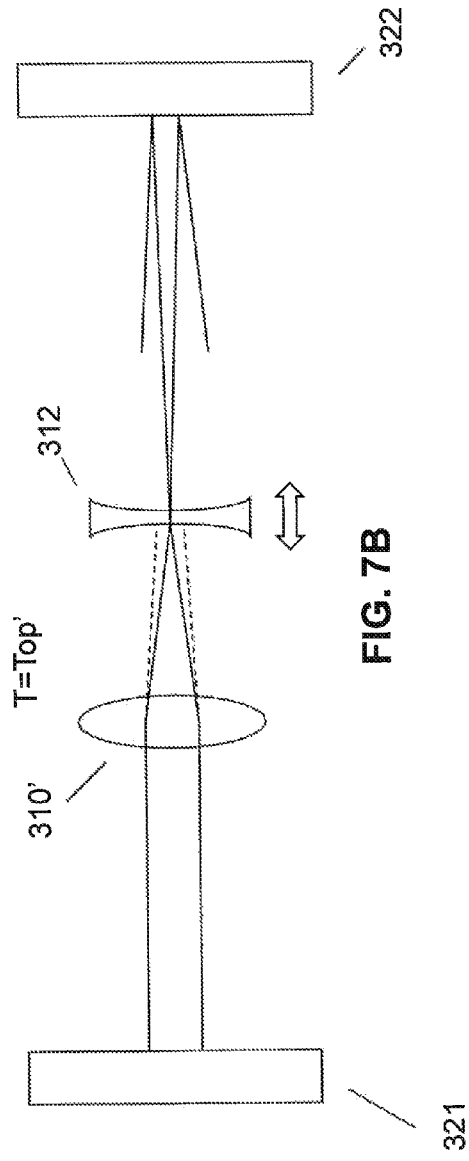

HIGH POWER FEMTOSECOND LASER WITH VARIABLE REPETITION RATE

CROSS REFERENCE TO RELATED APPLICATION

This application is a continuation of U.S. patent application Ser. No. 12/712,067, entitled "High power femtosecond laser with repetition rate adjustable according to scanning speed", by Michael Karavitis, incorporated herein in its entirety by reference.

TECHNICAL FIELD

This patent document relates to femtosecond lasers including adjustable repetition rate high power femtosecond lasers.

BACKGROUND

In many of today's ever more challenging laser applications there is a continued quest for shorter pulses which carry high energies per pulse. These features promise better control and greater operating speed for laser applications. A notable step in the evolution of the field was the appearance and maturation of laser systems outputting femtosecond laser pulses. These femtosecond lasers can be used for a wide variety of applications, including several different types of ophthalmic surgeries, where these ultra-short pulses can offer well-controlled tissue modification.

SUMMARY

Designs and techniques for constructing and operating femtosecond pulse lasers are provided in this document, including examples and implementations of laser systems with chirped pulse amplification, some of which have a low number of optical elements, some have a low frequency of malfunctions, others have a suitably small physical extent, yet others can allow the change of the repetition rates without substantial readjustments of the system, and some have reduced sensitivity for thermal lensing.

For example, some examples of a laser engine include an oscillator that generates and outputs a beam of femtosecond seed pulses, a stretcher-compressor that stretches a duration of the seed pulses, and an amplifier that receives the stretched seed pulses from the stretcher-compressor, amplifies an amplitude of selected stretched seed pulses to create amplified stretched pulses, and outputs a laser beam of amplified stretched pulses, wherein the stretcher-compressor receives the laser beam of amplified stretched pulses, compresses a duration of the amplified stretched pulses, and outputs a laser beam of femtosecond pulses with a pulse duration of less than 1,000 femtoseconds, and the amplifier includes a dispersion compensator that reduces a dispersion of the amplified stretched pulses.

In some examples the oscillator is a diode pumped fiber oscillator and outputs transform-limited seed pulses.

In some examples, the oscillator generates the beam with a seed-pulse-duration of less than 1,000 femtoseconds.

In some implementations the oscillator outputs the beam with a seed pulse repetition rate in the range of one of 10-100 MHz and 20-50 MHz.

In some implementations the stretcher-compressor includes a chirped volume Bragg grating.

In some implementations the stretcher-compressor includes a photothermal refractive glass.

In some implementations the stretcher-compressor stretches a duration of the femtosecond seed pulses by a factor greater than 10.

In some implementations the stretcher-compressor stretches a duration of the femtosecond seed pulses to a stretched duration of 1,000-200,000 femtoseconds.

In some implementations the laser engine does not contain a tunable stretcher-compressor.

In some implementations the laser engine includes a polarizer and a $\lambda/4$ plate between the oscillator and the stretcher-compressor that redirects the beam of stretched seed pulses toward the amplifier.

In some implementations the laser engine includes a Faraday isolator that receives the beam of stretched seed pulses from the stretcher-compressor, outputs the beam of stretched seed pulses toward the amplifier, receives the laser beam of amplified stretched pulses from the amplifier, outputs the laser beam of amplified stretched pulses towards a compressor port of the stretcher-compressor, and isolates the oscillator from the laser beam of amplified stretched pulses.

In some implementations the amplifier includes optical elements, and the dispersion compensator introduces a dispersion opposite in sign to a dispersion introduced by an optical element of the amplifier.

In some implementations the dispersion introduced by the dispersion compensator is essentially equal in magnitude and opposite in sign to a dispersion introduced within one roundtrip by the optical elements of the amplifier other than the dispersion compensator.

In some implementations the dispersion compensator includes at least one of a chirped mirror, a chirped fiber, a chirped grating, a prism, or a chirped transmissive optical element.

In some implementations the amplifier includes a gain material that amplifies the amplitude of the selected stretched seed pulses, two end-mirrors that define a resonant cavity, and two folding mirrors that fold a resonant optical pathway inside the amplifier, wherein at least one of the two end-mirrors and the two folding mirrors is a chirped mirror.

In some implementations the chirped mirror introduces a negative dispersion to the amplified stretched pulses.

In some implementations the laser engine is configured to output the laser beam with a first repetition rate, and subsequently with a different second repetition rate with essentially the same setup of all optical elements of the laser engine.

In some implementations the first repetition rate and the second repetition rate fall within one of the ranges of 10 kHz-2 MHz, 50 kHz-1 MHz, or 100 kHz-500 kHz.

In some implementations the laser engine can be modified to output the laser beam with the second repetition rate with essentially the same setup of all optical elements as with the first repetition rate, when the unmodified laser engine utilized different setups of the optical elements for the first and second repetition rates.

In some implementations the amplifier is configured to have a number of roundtrips of the amplified stretched pulses in the amplifier changed when a repetition rate is changed while keeping an optical setup of the amplifier unchanged.

In some implementations the amplifier has an end-mirror-to-end-mirror folded optical pathway of less than 1 meter.

In some implementations the amplifier is a cavity dumped regenerative amplifier, a chirped pulse amplifier or a Q-switched amplifier.

In some implementations the amplifier includes a switchable polarizer in an optical pathway between end-mirrors that can select stretched pulses by switching between a polarization-adjusting state in which the switchable polarizer adjusts a polarization of the amplified stretched pulses and a polarization-non-adjusting state in which the switchable polarizer essentially does not adjust the polarization of the amplified stretched pulses.

In some implementations the laser engine can include a high voltage power-switch that controls the switchable polarizer to switch from the polarization-non-adjusting state to the polarization-adjusting state with a rise time of less than 5 nanoseconds, 4 nanoseconds or 3 nanoseconds.

In some implementations the laser engine changes a first repetition rate of the laser beam of femtosecond pulses to a second repetition rate within one of 1-120 seconds, 10-60 seconds and 20-50 seconds.

In some implementations the laser engine changes a first repetition rate of the laser beam of femtosecond pulses to a second repetition rate within a changing time in the range of 1 µs-1 s.

In some implementations the amplifier includes at least one focusing mirror and a laser crystal, disposed in close proximity of a focal point of the focusing mirror.

In some implementations the laser engine is configured so that when a repetition rate of the laser engine is changed from a first value to a second value, both values in the range of 10 kHz-2 MHz, then the outputted laser beam's diameter changes by less than one of 10% and 20%, or the outputted laser beam's center moves by less than one of 20% and 40% of the beam's diameter.

In some implementations the femtosecond pulses of the laser beam have an energy in the range of one of 1-100 µJ/pulse, 10-50 µJ/pulse, or 20-30 µJ/pulse.

In some implementations the laser engine outputs a laser beam with a power greater than one of 0.1 W, 1 W or 10 W.

In some implementations the laser engine is part of an ophthalmic surgical system.

In some implementations a method of generating a laser beam with a laser engine includes the steps of: generating a beam of seed pulses with duration less than 1000 femtoseconds with an oscillator; stretching a duration of the seed pulses with a pulse stretcher; amplifying an amplitude of selected stretched seed pulses with an amplifier to generate amplified stretched pulses; compressing a duration of the amplified stretched pulses to below 1,000 femtoseconds with a pulse compressor; outputting a laser beam of femtosecond pulses with a first repetition rate in the range of 10 kHz-2 MHz and with a pulse duration less than 1,000 femtoseconds; changing the repetition rate from the first repetition rate to a second repetition rate in the range of 10 kHz-2 MHz without essentially changing an optical setup of the laser engine; and outputting the laser beam of femtosecond pulses with the second repetition rate and with a pulse duration less than a 1,000 femtoseconds.

In some implementations the amplifying step includes utilizing a dispersion compensator in the amplifier to reduce a dispersion of the amplified stretched pulses, caused by an optical component of the amplifier.

In some implementations the reducing the dispersion step includes introducing a compensating dispersion by at least one chirped mirror in the amplifier, wherein the compensating dispersion is essentially equal in magnitude and opposite in sign to a dispersion introduced by all optical elements of the amplifier other than the dispersion compensator per roundtrip.

In some implementations the changing the repetition rate step includes changing a number of roundtrips in the amplifier while keeping an optical setup of the amplifier essentially unchanged.

In some implementations the stretching step and the compressing step are executed by the same stretcher-compressor.

In some implementations outputting the laser beam with the second repetition rate within one of 1-120 seconds, 10-60 seconds or 20-50 seconds after having finished the outputting the laser beam with the first repetition rate.

In some implementations changing the repetition rate from the first repetition rate to the second repetition rate in a changing time in the range of 1 µs-1 s.

In some implementations a laser engine includes an oscillator that generates a pulsed light beam with a pulse duration of less than 1000 femtoseconds; a stretcher-compressor that stretches the duration of the pulses of the light beam; and an amplifier that amplifies an amplitude of the stretched light pulses to generate amplified stretched pulses, wherein the stretcher-compressor compresses a duration of the amplified stretched pulses, and outputs a beam of laser pulses; and the laser engine is operable to output the beam of laser pulses with a first repetition rate in the 10 kHz-2 MHz range and subsequently with a second repetition rate in the 10 kHz-2 MHz range, utilizing essentially the same setup of all optical elements of the laser engine, a duration of the laser pulses being less than 1000 femtoseconds for the first and the second repetition rates.

In some implementations the amplifier includes a dispersion compensator that at least partially compensates a dispersion introduced by optical elements of the amplifier.

In some implementations the amplifier includes a switchable polarizer between end-mirrors of the amplifier that switches between a state in which the switchable polarizer adjusts a polarization of the amplified stretched pulses; and a state in which the switchable polarizer does not adjust the polarization of the amplified stretched pulses with a rise time of less than one of 5 nanoseconds, 4 nanoseconds and 3 nanoseconds.

In some implementations the amplifier includes at least one focusing mirror; and a gain crystal, located near a focal point of the focusing mirror.

In some implementations the laser engine switches between the first repetition rate and the second repetition rate in a time less than one of 60 seconds, 1 second and 10 µs.

In some implementations a laser engine includes an oscillator that outputs femtosecond seed pulses; a stretcher that stretches a duration of the seed pulses; an amplifier that amplifies the stretched seed pulses into amplified stretched pulses, and includes a dispersion compensator to compensate a dispersion of the amplified stretched pulses induced by optical elements of the amplifier; and a compressor that receives the amplified stretched pulses, compresses a duration of the amplified stretched pulses, and outputs a laser beam of femtosecond pulses.

In some implementations a variable repetition rate laser engine includes a Q-switched cavity dumped regenerative amplifier; the amplifier including two end-mirrors, wherein the laser engine outputs femtosecond laser pulses; and a length of an optical pathway between the end-mirrors is less than 2 meters.

In some implementations the length of the optical pathway between the end-mirrors is less than 1 meter.

In some implementations the laser engine includes an oscillator that generates seed pulses which are transmitted to the amplifier, wherein a length of a total free-space optical path length from the point where photons of the seed pulses are generated in the oscillator to the point where the laser engine outputs the laser pulses is less than one of 500 meters, 300 meters, and 150 meters.

In some implementations all edge sizes of a cavity of the amplifier are less than one of 1 meter or 0.5 meter, wherein the cavity of the amplifier houses all optical elements of the amplifier.

In some implementations a footprint of the amplifier is less than one of 1 m$^2$ or 0.5 m$^2$.

In some implementations the laser engine includes a stretcher-compressor that includes a chirped volume Bragg grating.

In some implementations the amplifier includes a dispersion compensator that compensates a dispersion introduced by optical elements of the amplifier.

In some implementations the amplifier includes a laser crystal that amplifies an amplitude of lasing pulses; and two folding mirrors that fold a resonant optical pathway inside the amplifier, wherein at least one of the two end-mirrors and the two folding mirrors is a chirped mirror.

In some implementations the laser engine is configured to output a laser beam with a first repetition rate in a repetition rate range; and subsequently with a second repetition rate in the repetition rate range with essentially the same setup of all optical elements of the laser engine.

In some implementations the first and second repetition rates fall within a range of one of 10 kHz-2 MHz, 50 kHz-1 MHz or 100 kHz-500 kHz.

In some implementations the laser engine is configured so that the first repetition rate is changeable to the second repetition rate in a time less than one of 60 seconds, 1 second and 1 µs.

In some implementations the amplifier includes a switchable polarizer between the end-mirrors that switches in less than one of 5 ns, 4 ns, or 3 ns between a state in which the switchable polarizer adjusts a polarization of amplified pulses; and a state in which the switchable polarizer essentially does not adjust the polarization of the amplified pulses.

In some implementations the amplifier includes at least one focusing end-mirror; and a laser crystal, located in close proximity of a focal point of the focusing end-mirror.

In some implementations the laser engine includes an oscillator that generates and outputs a beam of femtosecond seed pulses; a stretcher-compressor that stretches a duration of the seed pulses; and an amplifier that receives the stretched seed pulses from the stretcher-compressor, amplifies an amplitude of selected stretched seed pulses to create amplified stretched pulses, and outputs a laser beam of amplified stretched pulses; wherein the stretcher-compressor receives the laser beam of amplified stretched pulses, compresses a duration of the amplified stretched pulses, and outputs a laser beam of femtosecond pulses with a pulse duration of less than 1,000 femtoseconds; wherein a length of an optical path length from the point where photons of the seed pulses are generated in the oscillator to the point where the laser engine outputs the laser pulses is less than 500 meters.

In some implementations the length of the optical path is less than 300 meters.

In some implementations a variable repetition rate laser engine includes an oscillator that generates and outputs a beam of femtosecond seed pulses; a stretcher-compressor that stretches a duration of the seed pulses; and a chirped pulse amplifier that amplifies an amplitude of selected stretched seed pulses to create amplified stretched pulses; wherein the amplifier includes a switchable polarizer with a switching time of less than 5 ns; the stretcher-compressor compresses a duration of the amplified stretched pulses to femtosecond values; and the laser engine occupies an area of less than 1 m$^2$.

In some implementations the laser engine is part of a surgical laser system, the surgical laser system having the laser engine and an imaging system on a top deck of the surgical laser system.

In some implementations a variable repetition rate laser engine includes an oscillator that generates and outputs a beam of femtosecond seed pulses; an integrated stretcher-compressor that stretches a duration of the seed pulses; and a Q-switched cavity dumped regenerative amplifier that amplifies an amplitude of selected stretched seed pulses to create amplified stretched pulses; wherein the stretcher-compressor compresses a duration of the amplified stretched pulses to output femtosecond laser pulses, and a number of optical elements of the laser engine is less than 75.

In some implementations the number of optical elements of the laser engine is less than 50.

In some implementations the number of optical elements of the laser engine in portions other than an oscillator is less than 50.

In some implementations the number of optical elements of the laser engine in portions other than the oscillator is less than 35.

In some implementations an optical element is one of: a mirror, a lens, a parallel plate, a polarizer, an isolator, any switchable optical element, a refractive element, a transmissive element, or a reflective element.

In some implementations an optical element has the light entering from air and exiting into air.

In some implementations the integrated stretcher-compressor includes a chirped volume Bragg grating.

In some implementations the amplifier includes a dispersion compensator that compensates a dispersion introduced by optical elements of the amplifier.

In some implementations the amplifier includes two end-mirrors, defining a resonant cavity; and two folding mirrors that fold a resonant optical pathway inside the amplifier, wherein at least one of the two end-mirrors and the two folding mirrors is a chirped mirror.

In some implementations the laser engine is configured to output a laser beam with a first repetition rate in a repetition rate range; and subsequently with a second repetition rate in the repetition rate range with essentially the same setup of all optical elements of the laser engine, wherein the first and second repetition rates are within a range of one of 10 kHz-2 MHz, 50 kHz-1 MHz, or 100 kHz-500 kHz.

In some implementations the laser engine is configured so that the first repetition rate is changeable to the second repetition rate in a changing time less than 1 second.

In some implementations the amplifier includes a switchable polarizer between the end-mirrors that can switch in less than one of 5 ns, 4 ns, and 3 ns between a state in which the switchable polarizer adjusts a polarization of the amplified stretched pulses; and a state in which the switchable polarizer essentially does not adjust the polarization of the amplified stretched pulses.

In some implementations the amplifier includes at least one focusing mirror; and a laser crystal, located in close proximity of a focal point of the focusing mirror.

In some implementations a laser engine includes an oscillator that generates and outputs a beam of femtosecond seed pulses; a stretcher-compressor that stretches a duration of the seed pulses; and an amplifier that receives the stretched seed pulses from the stretcher-compressor, amplifies an amplitude of selected stretched seed pulses to create amplified stretched pulses, and outputs the amplified stretched pulses; wherein the stretcher-compressor receives the amplified stretched pulses, compresses a duration of the amplified stretched pulses, and outputs a laser beam of femtosecond pulses with a pulse duration of less than 1,000 femtoseconds; wherein a number of optical elements of the laser engine in portions other than the oscillator is less than 50.

In some implementations a number of optical elements of the laser engine is less than 75.

In some implementations a method of scanning with a laser system includes the steps of generating laser pulses having a variable repetition rate with a laser engine; focusing the laser pulses to a focus spot in a target region with a scanning laser delivery system; scanning the focus spot with a scanning speed in the target region with the scanning laser delivery system; changing the scanning speed; and adjusting the repetition rate according to the changed scanning speed with a repetition-rate controller.

In some implementations the generating step includes generating femtosecond seed pulses by an oscillator; stretching the seed pulses by a stretcher-compressor; amplifying selected stretched seed pulses into amplified stretched pulses by an amplifier; and compressing the amplified stretched pulses into femtosecond laser pulses by the stretcher-compressor.

In some implementations the method includes adjusting the repetition rate to approximately maintain a density of laser-generated bubbles in the target region around a selected value.

In some implementations the density of bubbles is one of a linear density, an areal density or a volume density.

In some implementations the adjusting the repetition rate step includes adjusting the repetition rate proportionally to the scanning speed.

In some implementations the adjusting the repetition rate step includes adjusting the repetition rate from a first value to a second value in a time in the range of 1 µsec-1 sec.

In some implementations the scanning the focus spot step includes scanning the focus spot along a minimal acceleration path.

In some implementations the method includes XY scanning the focus spot along a switchback path; and slowing down the repetition rate when approaching the switchback portion of the path.

In some implementations the method includes scanning the laser beam along a spiral; and slowing down the repetition rate when the scanning approaches the center of the spiral.

In some implementations the adjusting the repetition rate includes receiving information by the repetition-rate controller about the changed scanning speed by one of sensing the changing scanning speed, and getting electronic information about the changing scanning speed from a processor or a memory and adjusting the repetition rate according to the received information about the changed scanning speed.

In some implementations a variable repetition rate laser scanning system includes an oscillator that generates and outputs a beam of femtosecond seed pulses; a stretcher-compressor that stretches a duration of the seed pulses, receives amplified stretched pulses from an amplifier, compresses a duration of the amplified stretched pulses, and outputs a laser beam of femtosecond pulses with a repetition rate; the amplifier that receives the stretched seed pulses from the stretcher-compressor, amplifies an amplitude of selected stretched seed pulses to create amplified stretched pulses, and outputs the amplified stretched pulses towards the stretcher-compressor; and a scanning optics that scans a focal spot of the laser beam in a target region with a variable scanning speed to generate spots of photodisruption; wherein the laser scanning system changes the repetition rate to create the spots of photodisruption with a predetermined density profile.

In some implementations the amplifier includes a dispersion compensator that reduces a dispersion of the amplified stretched pulses.

In some implementations the amplifier includes a switchable polarizer that rotates a polarization plane of the stretched pulses in the amplifier, wherein a rise time of the switchable polarizer is less than one of 5 ns, 4 ns, or 3 ns.

In some implementations the laser scanning system includes a control electronics that applies control signals to the switchable polarizer to cause the switchable polarizer to switch with a rise time of less than one of 5 ns, 4 ns, and 3 ns.

In some implementations a method of scanning with a laser engine includes the steps of generating femtosecond laser pulses with a repetition rate; focusing the laser pulses to a focus spot in a target region to generate spots of photodisruption; scanning the focus spot in the target region with a scanning speed; and adjusting the repetition rate during the scanning to create spots of photodisruption with a density profile.

In some implementations the adjusting step includes creating the spots of photodisruption with one of a linear spot density, an areal spot density and a volume spot density being kept essentially even in a target region.

In some implementations the adjusting step includes adjusting the repetition rate according to a variation of the scanning speed.

In some implementations the adjusting step includes adjusting the repetition rate proportionally to the scanning speed.

In some implementations the adjusting the repetition rate step includes adjusting the repetition rate from a first value to a second value in a time in the range of 1 µsec-1 sec.

In some implementations the generating step includes generating femtosecond seed pulses by an oscillator; stretching the seed pulses by a stretcher-compressor; amplifying selected stretched seed pulses into amplified stretched pulses by an amplifier; and compressing the amplified stretched pulses into femtosecond laser pulses by the stretcher-compressor.

In some implementations the scanning the focus spot step includes scanning the focus spot along a minimal acceleration path.

In some implementations the method includes scanning the focus spot along a switchback path; and slowing down the repetition rate when approaching the switchback portion of the path.

In some implementations the method includes scanning the laser beam along a spiral; and slowing down the repetition rate according to the scanning approaching the center of the spiral.

In some implementations the method includes scanning the laser beam along one of an end of a line and a corner of a line; and slowing down the repetition rate according to the scanning approaching one of the end of the line and corner of the line.

In some implementations the method includes receiving stored or sensed information about the scanning speed, and adjusting the repetition rate according to the received information regarding the scanning speed.

In some implementations the method includes receiving sensed or imaged information about the target region, and adjusting the repetition rate according to the received information regarding the target region.

In some implementations, a laser engine can include an oscillator that outputs femtosecond seed optical pulses and an amplifier that amplifies seed optical pulses to produce amplified optical pulses. This amplifier includes an optical cavity that is coupled to receive and circulate the seed optical pulses, and an optical switch device coupled to the optical cavity to control coupling of the light of the received seed optical pulses into the optical cavity and to control coupling of light inside the optical cavity out as output light of the amplifier. The optical switch device is configured to control and adjust a number of roundtrips of the light coupled inside the optical cavity to control and adjust a pulse repetition rate of the amplified optical pulses produced by the amplifier. The amplifier also includes an optical gain medium inside the optical cavity to amplify the seed optical pulses into amplified optical pulses, and a dispersion compensator inside the optical cavity to compensate a dispersion of the amplified optical pulses induced by the amplifier. The laser engine includes one or more optical elements outside the amplifier to stretch a duration of the seed optical pulses before each seed optical pulse is coupled into the amplifier and to compress a duration of the amplified optical pulses outputted by the amplifier to produce the amplified optical pulses. The laser engine can be configured to be free of a dispersion compensation device outside the amplifier that is provided for compensating the dispersion of the amplified optical pulses induced by the amplifier.

In yet other implementations, a method for operating a laser engine to produce femtosecond optical pulses can include stretching femtosecond seed optical pulses to produce stretched seed optical pulses with reduced optical power in each pulse; and coupling the stretched seed optical pulses into an optical cavity of an optical amplifier to amplify optical power of each stretched seed optical pulse to produce amplified stretched optical pulses. Inside the optical amplifier, an optical compensator is used to provide dispersion compensation to each optical pulse, where the optical compensator is structured to introduce a dispersion that is opposite in sign and is substantially equal in magnitude with a dispersion induced by the amplifier within one roundtrip of light inside the optical cavity of the amplifier, excluding the dispersion caused by the dispersion compensator. This method includes operating an optical switch device coupled to the optical cavity to control coupling of light of the stretched seed optical pulses into the optical cavity and coupling of light of the amplified stretched optical pulses out of the optical cavity; compressing a pulse duration of the amplified stretched optical pulses out of the optical cavity to produce compressed amplified optical pulses as output of the laser engine; and operating the optical switch device to control and adjust a number of roundtrips of light inside the optical cavity to control and adjust a pulse repetition rate of the compressed amplified optical pulses, without using a dispersion compensation device, that is located outside the amplifier, to compensate the dispersion induced by the amplifier.

BRIEF DESCRIPTION OF DRAWINGS

FIGS. 1A-B illustrate two embodiments of a high power femtosecond laser engine 1.

FIGS. 5A-B illustrate the pump-gain-dump cycle of a laser cavity.

FIGS. 7A-B illustrate design challenges relating to thermal lensing at two different temperatures of the laser crystal 310 in the amplifier 300.

DETAILED DESCRIPTION

Figure 2:
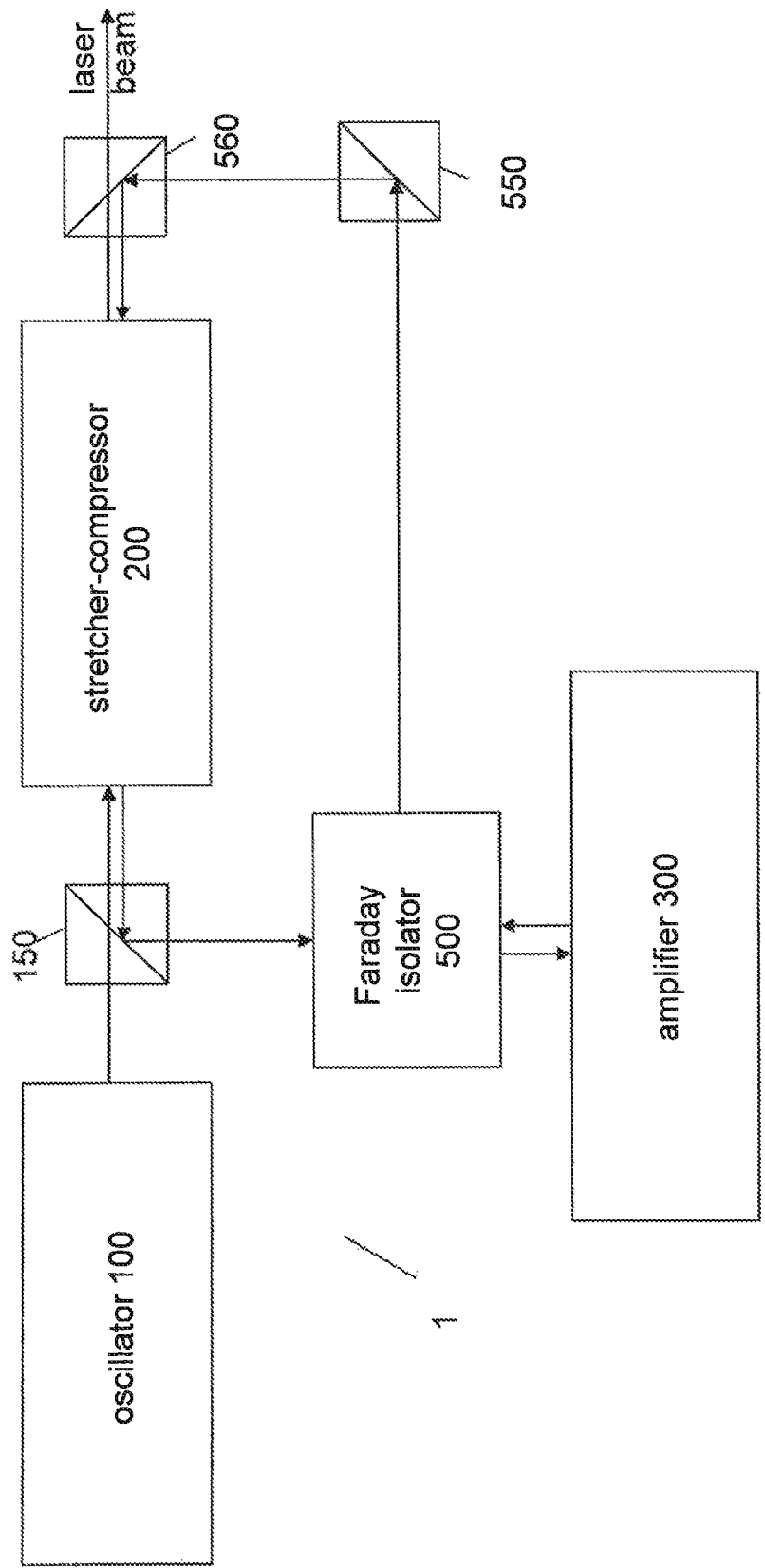
FIG. 2 illustrates an embodiment of the high power femtosecond laser engine 1 in more detail.

In early femtosecond lasers the extreme shortness of the pulse length lead to an extreme high power in these pulses. This high power, however, threatened to damage the gain medium of the lasers. The solution arrived in the form of chirped pulse amplification (CPA). In this technology femtosecond seed pulses are generated, then the length of the seed pulses is stretched by a factor of 10-1000 to the picosecond range, thus drastically reducing the power within a pulse. These stretched pulses can be safely amplified with the gain medium without causing damage. The amplification is followed by a compression, compressing the length of the amplified pulses back to femtoseconds. This CPA approach has been introduced into numerous applications today.

However, CPA lasers have drawbacks as well. Typically, these lasers have a large number of optical elements and are correspondingly quite complex. These factors make the frequency of malfunction quite high and reduce the number of times the lasers can be reliably switched on and off. Also, the unusually large size of the CPA lasers makes their integration into medical devices very challenging, since those are typically used in the confined spaces of surgical suites or operating rooms. Moreover, if different procedures call for changing the repetition rate of the pulses, this change requires performing time-consuming readjustments of the large number of optical elements. In addition, thermal lensing impacts the optical performance of most CPA lasers substantially, making them quite sensitive to the operating power of the laser. This sensitivity is a further obstacle against repetition rate changes.

Laser designs and techniques for constructing and operating femtosecond pulse lasers described in this document can be implemented to address various technical issues in other femtosecond pulse lasers as well.

FIG. 1A illustrates a chirped pulse amplification (CPA), or cavity dumped regenerative amplifier (CDRA) laser engine 1, which includes an oscillator 100, a stretcher-compressor 200, and an optical amplifier 300.

The oscillator 100 can generate and output a beam of femtosecond seed pulses. The stretcher-compressor 200 can stretch a duration of these seed pulses. The amplifier 300 can receive the stretched seed pulses from the stretcher-compressor 200, amplify an amplitude of the stretched pulses, and output a laser beam of amplified stretched pulses. These amplified stretched pulses can be optically coupled back into the stretcher-compressor 200, which can compress a duration of the amplified stretched pulses and output a laser beam of femtosecond pulses.

FIG. 1B illustrates an example of another CPA laser engine 1' where an optical amplifier 300' downstream from an optical oscillator 100' and an optical pulse stretcher 200' can optically couple the amplified stretched pulses into a separate compressor 400, which can compress the amplified stretched pulses and output a laser beam of femtosecond pulses.

The description of the laser engines 1 and 1' contains many control functions and method steps. These functions and steps can be controlled by one or more controllers, processors and other computer-controllers. These controllers, processors and computer-controllers can utilize advanced software, interacting with each other. For clarity of presentation, these processors, controllers and their corresponding software are suppressed in the figures of this patent document, but are meant to be part of the description of the laser engines 1 and 1' in some implementations.

While several of the examples in this application will be described in terms of ophthalmic applications, such as cataract surgery, capsulotomy or corneal procedures, implementations of the laser engine 1 can be used in a remarkably wide range of applications, which include a wide variety of ophthalmic procedures, such as retinal and corneal surgery, as well as dermatological and dental applications, different surgical applications, and various material machining applications, which shape a piece of material with laser photodisruption or some other laser aided process.

As indicated above, there are various shortcomings of some chirped pulse amplification CPA/CDRA laser engines. Embodiments of the laser engine 1 can be configured to offer solutions to these problems by employing some or all of the following design principles as well as other design considerations:

(1) Many lasers have a large number of optical elements, such as a hundred or more, making their design complex and pricey. In this context, embodiments of the laser engine 1 can have as few as 50 optical elements altogether, and no more than 35 optical elements outside the oscillator 100.

(2) Lasers with a large number of optical elements and with the corresponding complexity can have a high frequency of malfunctions. In some CPA/CDRA lasers the probability of malfunction can became quite high after the laser was "cycled", i.e. switched on and off 30-40 times. Such systems may require preventive maintenance after 30-40 switching cycles or more often to preempt an actual malfunction from occurring during the regular operation of the laser.

In this context, because of the much-reduced number of optical elements and novel dispersion control solutions, embodiments of the laser engine 1 can be cycled 100, 120 or more times with the expectation of regular operation, thus greatly reducing the frequency of required servicing and increasing overall reliability.

(3) The large physical extent and the corresponding long duration of the roundtrips of some CPA/CDRA lasers translates to long recharge times as described below, thus limiting their repetition rates, as well as their utility for being used in space limited surgical devices.

In this context, embodiments of the laser engine 1 can have a compact resonant cavity, which can have an end-mirror-to-end-mirror optical pathway shorter than one meter in some embodiments and two meters in others. The compactness is also a factor contributing to the high repetition rates of the laser engine 1, which can be as high as 300, 500 or even 1,000 kHz.

The above compactness can translate to an overall optical pathway measured from the point of generation of the photon to the point of exit and including all the roundtrips in the cavity, to be as low as 150 meters in spite of the high repetition rate of these lasers.

(4) Some CPA/CDRA lasers are finely tuned for operating at a specific repetition rate. This tuning can involve compensating the dispersion of the stretcher 200 and the amplifier 300 at the specific repetition rate by the compressor 200/400. However, if an application calls for changing the repetition rate, the stretcher and the amplifier causes a different dispersion at this new repetition rate, upsetting the finely tuned dispersion-compensation of the CPA/CDRA laser. To compensate this changed dispersion, typically the optical elements of the stretcher 200 and the compressor 200/400 need to be readjusted in a time-consuming procedure. This readjustment makes it technically cumbersome to change the repetition rate of these CPA/CDRA lasers on the time scales of the ophthalmic surgical procedures. Therefore, most commercial ophthalmic CPA lasers do not offer the functionality of a variable repetition rate, and none offer a changeable repetition rate during surgical procedures.

In this context, embodiments of the laser engine 1 can include a dispersion controller or dispersion compensator that can reduce and even minimize a dispersion of the laser beam caused by the amplifier 300. This minimization of the dispersion allows the changing of the repetition rate without a time-consuming readjustment of the optical elements of the laser engine 1. Therefore, the inclusion of the dispersion controller makes it possible to change the repetition rate during time sensitive surgical procedures. An example is to use a first repetition rate for a cataract surgery and a second repetition rate for a capsulotomy or a corneal procedure. As it is well known, in these surgeries the time factor is quite crucial.

(5) In some cases, within a surgical procedure cut-patterns may be used to place the laser spots with an uneven density when the laser beam has fixed repetition rates. Examples include slowing down a scanning speed around a turning point of a raster or scanning pattern, or in a narrowing or a broadening spiral.

In this context, embodiments of the laser engine 1 can be configured to have an essentially continuously adjustable repetition rate and to adjust the repetition rate near-synchronously with the changing scanning speed to compensate the variations of the scanning speed, allowing the formation of laser spots with a near constant density or with a predetermined density profile.

(6) In addition, thermal lensing negatively impacts the optical performance of some CPA/CDRA lasers and makes them undesirably sensitive to changes in the power and repetition rate of the laser beam. In this context, embodiments of the laser engine 1 can utilize thermal lensing compensation techniques, making these embodiments quite insensitive to changes in the power and repetition rate of the applied laser beam.

FIG. 2 illustrates a specific implementation of the laser engine 1 in detail. The oscillator 100 can be a wide variety of light sources which can generate and output seed pulses for the laser engine 1. Examples include diode pumped fiber oscillators. The oscillator may include a single diode, e.g. a GaAs diode operating at an 808 nm wavelength, or a large variety of other diodes.

Fiber oscillators are much smaller than oscillators based on free space beam propagation. In surgical applications, where the crowdedness of the operating theatre is a pressing constraint, reducing the spatial extent of the laser engine is a highly prized design feature.

In some examples, the oscillator outputs high quality seed pulses. Several factors can contribute to the high pulse quality as detailed next.

(i) In some embodiments the diode can include a frequency stabilizing bar, such as a volume Bragg grating inside the diode. Such gratings can provide pulses with low noise and high pulse-to-pulse stability. The fiber may be formed of glass doped by Nd or Yb.

(ii) The oscillator 100 can include a semiconductor saturable absorber mirror, or SESAM. Utilizing one or more SESAMs improves the coherence of the modes within the generated pulses, resulting in an essentially mode-locked operation.

Oscillators with the above design principles can output essentially transform-limited seed pulses, e.g. with a Gaussian shape. In some examples, flat-top pulses may be also generated. The pulse-duration can be less than 1,000 femtoseconds (fs). In some implementations, the pulse duration can be in the 50-1,000 femtoseconds range, in some other embodiments in the 100-500 femtoseconds range. The seed pulse frequency, or repetition rate can be in the range of 10-100 MHz, in other embodiments in the range of 20-50 MHz. Decreasing the seed pulse frequency below 10 or 20 MHz raises a series of design challenges though. For this reason, most oscillators operate at frequencies above 20 MHz.

The power of the beam of seed pulses can be in the range of 10-1000 mW, in other embodiments in the range of 100-200 mW.

For many timing considerations, the oscillator 100 can be used as a master clock.

The stretcher-compressor 200 can stretch the seed pulses by introducing different delay times for the different frequency-components of the pulse. In short, the stretcher-compressor can introduce a dispersion or chirp.

Figure 3A:
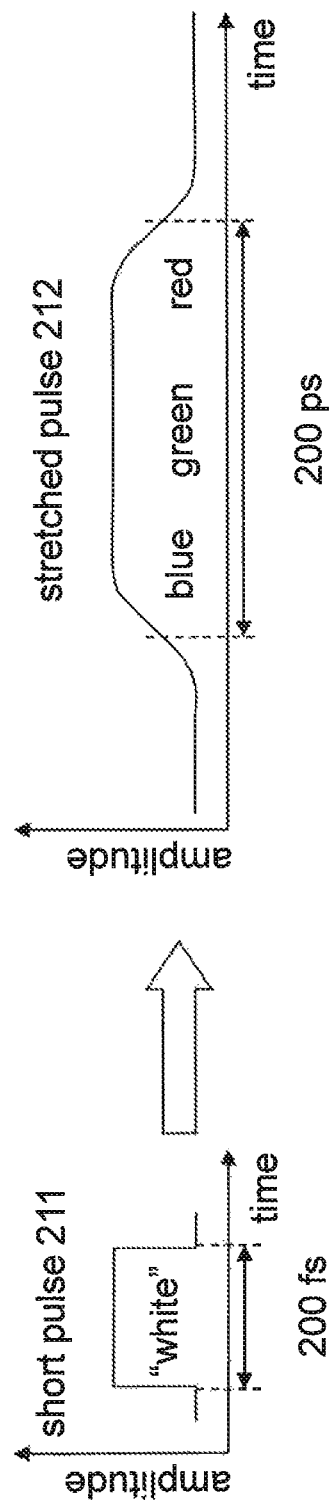
FIG. 3A illustrates the concept of chirping a laser pulse.

FIG. 3A illustrates this chirp in detail. The stretcher-compressor 200 may receive a short pulse, whose frequency content, or spectrum, is approximately uniform, or "white", across most of the duration of the pulse. In other words, the amplitude of the different frequency components at the beginning of the pulse is approximately even and remains so during the duration of the pulse. The stretcher-compressor 200 can stretch the pulse length by introducing different delay times for the red, green and blue components of such "white" pulses. Therefore, the frequency content, or spectrum, of the pulse outputted by the stretcher-compressor 200 can become time dependent. According to a typical convention, pulses where the leading part is dominated by the red frequencies while the trailing portion is dominated by blue frequencies are referred to as having a positive dispersion or chirp.

The present description refers to chirp in the time domain, i.e. to the relative delay of the high and low frequency components. Spatial chirp, i.e. the separation of high and low frequency components spatially within the beam raises a variety of additional design challenges and is not among the desired functionalities of the stretcher 200' or stretcher-compressor 200.

The stretcher-compressor 200 or the stretcher 200' can introduce a positive chirp into initially white seed pulses by enhancing the red content in the leading portion of the pulse and enhancing the blue content in the trailing portion of the pulse. Analogously, non-white pulses can also be chirped by the stretcher-compressor 200 or the stretcher 200'.

The stretcher-compressor 200 may stretch a duration of the femtosecond seed pulses from a range of 50-1,000 femtoseconds to a stretched duration of 1,000-200,000 femtoseconds, or 1-200 picoseconds or even up to 500 ps. The stretcher-compressor 200 can stretch a duration of the femtosecond seed pulses by a factor greater than 10. In some cases, the stretching factor can be greater than $10^2$, $10^3$, $10^4$, or $10^5$. Each of these stretching factors introduces different design criteria for the amplifier 300.

Figure 3B:
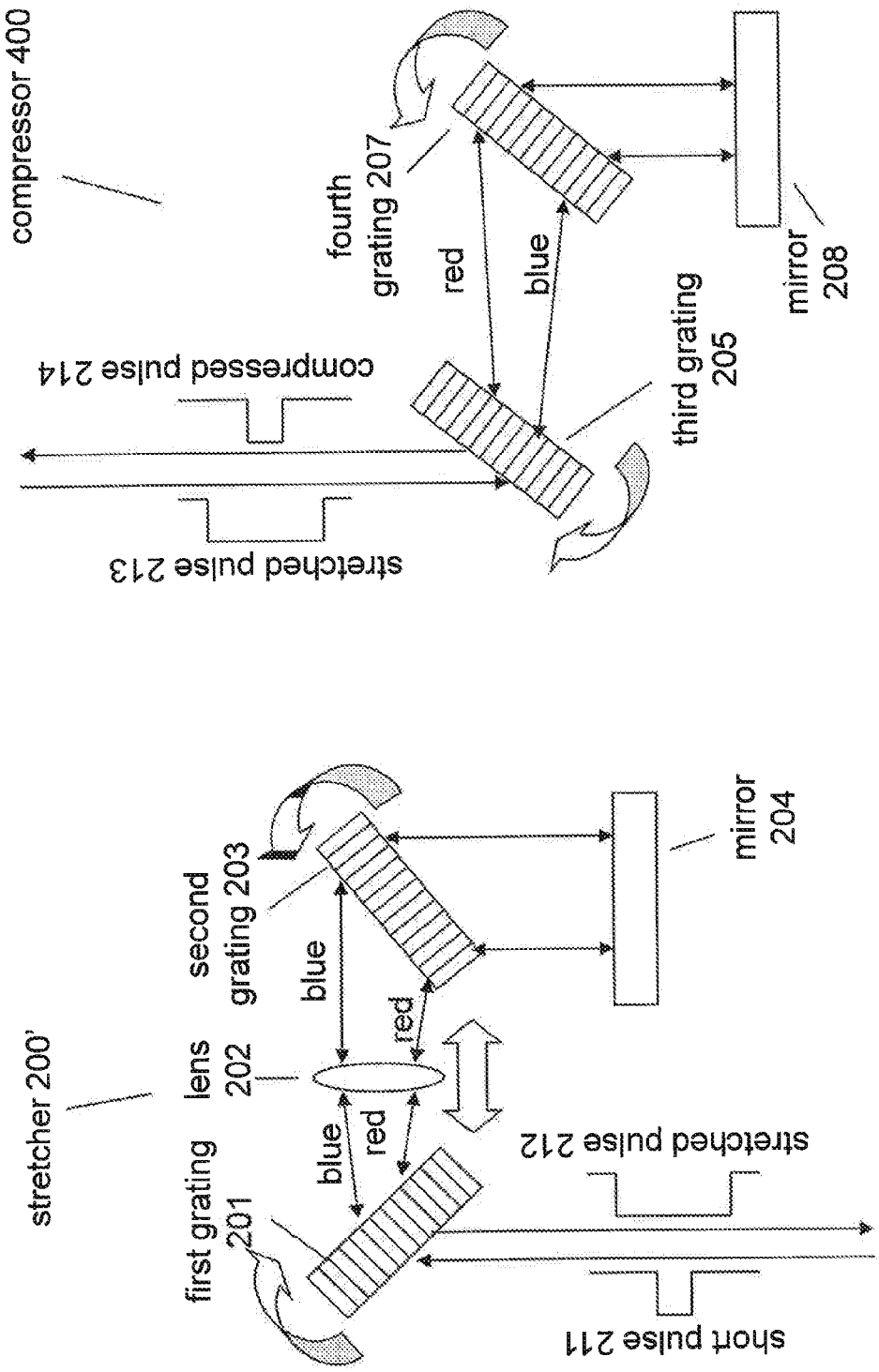
FIG. 3B illustrates an example of a stretcher 200' and a compressor 400.

FIG. 3B illustrates that the laser engines 1' of the type shown in FIG. 1B can utilize a stretcher 200' and a separate compressor 400. The stretcher 200' can include a first grating 201, a lens 202, a second grating 203, and a mirror 204. When a short pulse 211 enters the stretcher 200', the first grating 201 can refract the different frequency components into different directions. Upon exiting the first grating 201, the diverging rays may propagate to the lens 202 and get redirected to the second grating 203. Some embodiments may use two lenses in place of the lens 202. Since the second grating 203 makes an angle with the first grating 201 and the different frequency rays propagate in diverging directions, the different frequency components travel different distances, needing different times to do so.

For example, in the stretcher 200' of FIG. 3B the components with frequencies in the blue region of the spectrum travel a longer distance than the components in the red region, acquiring a delay relative to the red component of the incident short pulse. Here and throughout, the terms "blue" and "red" are used in an illustrative and relative manner. They refer to the components of the pulse spectrum with shorter and longer wavelengths, respectively. In particular implementations, the laser mean wavelength can be in the 1000-1100 nm and the bandwidth of the pulse can be in the range of 2-50 nm, in some cases in the range of 5-20 nm. In this example the entire spectrum of the pulse is in the infrared region. In this example, the terms "blue" and "red" refer to the portions of the infrared spectrum which have shorter and longer wavelengths within the bandwidth of the pulse, respectively.

The functions of the second grating 203 include the partial control of the chirp, i.e. the delay of the blue component relative to the red component as well as the restoration of the beam to an essentially parallel beam to make it suitable for reflection by the mirror 204. The mirror 204 reflects the frequency-separated parallel rays, which then retrace their optical path through the second grating 203, the lens 202 and the first grating 201. By the time the pulse exits the first grating 201, the blue component of the pulse travels considerably longer distance and thus lags behind the red component.

This delay has at least three effects on the outputted pulse: (i) the pulse length gets considerably longer, (ii) the amplitudes of the different frequency-components are shifted relative to one another in time, shifting the red components to the leading edge of the pulse and the blue components to the trailing edge, or vice versa, (iii) the total energy of the pulse is distributed over a longer pulse length, reducing the optical power of the outputted pulse. In some cases, the pulse duration can be stretched by a factor of 100, 1000 or more, the power correspondingly can be reduced by a factor of a 100, 1000, or more. In sum, the stretcher-compressor 200 or the stretcher 200' can stretch the pulse, introduce a positive chirp and thereby substantially reduce the power of the pulse.

As described earlier, reducing the peak power of the pulse is a beneficial aspect of the CPA/CDRA lasers as the cavity optics of the subsequent amplifier 300 are not exposed to pulses of excessively high power and thus avoid getting damaged by the beam.

FIG. 3B also illustrates an example of a compressor 400, which can include a third grating 205, a fourth grating 207 and a mirror 208. Some examples have no lens between these gratings, while others may have one or two lenses. The third grating 205 again directs different components of the pulse spectrum in different directions in analogy with the first grating 201 of the stretcher 200'. The fourth grating 207 again partially controls the relative delays of the blue and red components through its orientation, in analogy with the second grating 203. However, since the fourth grating 207 is now oriented opposite to the second grating 203, the optical pathway of the blue components is now shorter, causing a negative chirp. This negative dispersion allows the blue components of the stretched pulse to catch up with the red components, shortening the overall duration of the amplified stretched pulses from hundreds of picoseconds to hundreds of femtoseconds. Designs with the separate stretchers 200' and compressor 400 are embodiments of the laser engine 1' of FIG. 1B.

FIG. 3B also illustrates two sensitive aspects of the designs of FIG. 1B, having a separate stretcher 200' and compressor 400.

(i) First, the stretcher 200', the amplifier 300 and the compressor 400 need to be fine tuned with each other, so that the compressor 400 can undo the stretching caused by the stretcher 200' and the subsequent dispersion caused by the amplifier 300 with high precision. Therefore, setting the location of the lens 202 and the orientation of the first to fourth gratings 201-207 may require especially high precision to compensate the dispersion of the amplified stretched pulses and to compress them back to femtosecond pulses. And, of course, high precision adjustments are quite sensitive to perturbations: small changes in temperature, number of roundtrips, and mechanical stress can undermine the precision adjustment, requiring maintenance and re-calibration of the laser engine 1' with the architecture of FIG. 1B.

(ii) In some complex or multi-step procedures, the change of the repetition rate may be desirable. However, such a change of the repetition rate is typically accompanied by a change of the number of roundtrips to optimize the outputted pulses. In turn, the change of the number of roundtrips often causes a change in the thermal lensing as well as the compounded dispersion caused by the amplifier 300. Therefore, the change of the repetition rate and the number of roundtrips can upset the carefully calibrated balance of the stretching, dispersion and compression.

To counteract these changes, as shown by the arrows of FIG. 3B, some implementations of the laser engine 1' might be recalibrated by changing the location of the lens 202, the position or the orientation of some of the gratings 201, 203, 205 and 207, the location of the mirrors 204 and 208, or the location where the beam hits the lens 202 by moving one or more mirrors. Needless to say, these changes typically require cautious and often iterative mechanical adjustments and precision calibration, all of which are time consuming interventions.

The slowness of the recalibration can pose a problem in applications where a timely change of the pulse-repetition rate is desired. This can be especially prohibitive in applications where time is a critical factor, e.g. during ophthalmic surgical applications, where the patient's ability to control eye movements may be as low as 90 seconds. For all of these reasons, most laser engines do not offer the functionality of a changeable repetition rate.

In addition, since in the laser engine 1' the stretcher 200' is separate from the compressor 400 and both of them include multiple gratings and lenses, the spatial extent of the stretcher and compressor of the laser engine 1' of the type in FIG. 1B is typically spatially quite extensive.

To reduce the spatial footprint of the stretcher 200' and the compressor 400, as well as to reduce calibration times, in some implementations of the laser engine 1', the stretcher 200' and the compressor 400 can share one or more optical elements. In some cases, they can share a grating, such as the first grating 201 and the third grating 205 can be the same.

In some multiply folded examples the two gratings of the stretcher 200' can be the same physical grating, the lenses and mirrors directing the beam on the same grating from different directions during different passes. In some multiply folded examples, all functions of the two gratings of the stretcher 200 and the two gratings of the compressor 400 can be performed by a single shared grating.

Figure 3C:
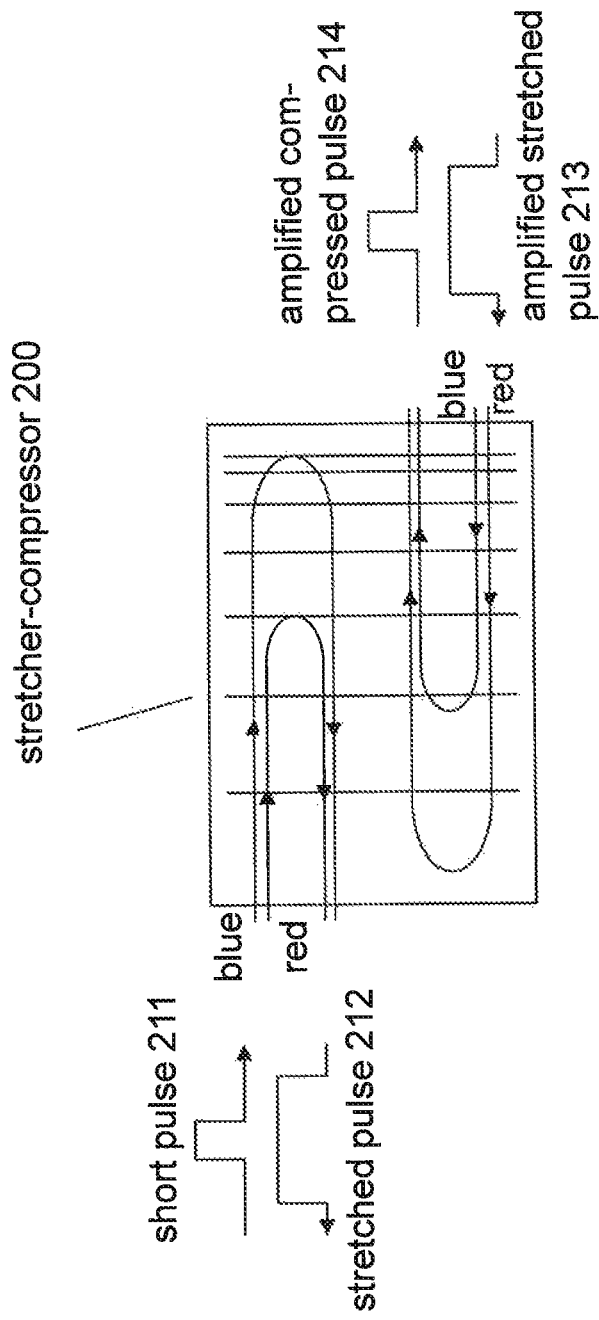
FIG. 3C illustrates an implementation of an integrated stretcher-compressor 200.

FIG. 3C illustrates an example of the stretcher-compressor 200 of the embodiment of FIG. 1A, which offers a robust solution to these challenges. The stretcher-compressor 200 of FIG. 3C integrates the stretching and the compressing functionalities, and thus it can be employed in an embodiment of the laser engine 1 of FIG. 1A. This stretcher-compressor 200 as implemented in the example in FIG. 3C is a chirped volume Bragg grating (CVBG). This CVBG can be a stack of layers, e.g., in a photothermal refractive (PTR) glass, the layers having suitable indices of refraction and a grating period that varies with the position of the layers. In such a design the Bragg resonance condition occurs at different positions for different spectral components of a pulse. Thus, different spectral components are reflected at different locations, acquiring different time delays within the pulse.

As shown in the example in FIG. 3C, when a short "white" pulse 211 enters the stretcher-compressor 200, the red frequency components get refracted from the near regions with wider layer spacings or grating periods, since their wavelength is longer and satisfies the Bragg reflection conditions in these near regions. In contrast, the blue frequency components, having shorter wavelengths, are returned from the farther regions of the grating. Since the blue components traverse a longer optical path, they acquire a delay relative to the red components. Thus, the inputted short white pulse 211 is stretched by this CVBG stretcher-compressor 200 into a longer stretched pulse 212. In the specific example, the stretched pulse 212 develops a positive chirp because the blue components are delayed relative to the red components. Other implementations can have a CVBG producing a negative chirp, delaying the red spectral components relative to the blue ones.

This CVBG stretcher-compressor 200 can also compress the amplified stretched pulses 213 with high precision without any cumbersome fine tuning, since the stretched pulses, after amplification by the amplifier 300, are injected into the same CVBG stretcher-compressor 200 from the opposite end, or compressor port. When a stretched pulse enters the CVBG stretcher-compressor 200 from the opposite end, its red components are delayed to the same degree as its blue components were delayed during the stretching step, restoring the original short length of the pulse. Therefore, this stretcher-compressor 200 can compensate the dispersion introduced during the stretching very efficiently and output a properly compressed amplified pulse 214.

In comparison to the particular aspects of laser engines 1' with separated stretcher 200' and compressor 400, (i) the laser engine 1 is not highly sensitive to the precise alignment of moving optical elements since it has none, and thus shows a remarkable robustness against mechanical perturbations or changes of the operating temperature, and (ii) since the novel design of the amplifier 300 does not induce additional dispersion in relation to the number of roundtrips as explained further in relation to Eqs. (1)-(2) and FIGS. 5A-B, the laser engine 1 does not require sensitive recalibration and re-alignments of its optical elements and setup when the repetition rate is changed. These attributes enable the use of the laser engine 1 in applications where a fast or timely change of the repetition rate is important.

In other designs different from what is described above, the amplifier 300 can introduce additional dispersion. In these designs the integrated architecture of the stretcher-compressor 200 can be supplemented with a re-adjusting functionality as the compressor has to compress not only the dispersion of the stretcher, but the additional dispersion of the amplifier 300. This added task might require implementing a tunable block in relation to the compressor functionality.

Returning to FIG. 2, the laser engine 1 can further include an effective polarizing beam splitter 150. Beam splitter 150 can include a polarizer and a λ/4 plate between the oscillator 100 and the stretcher-compressor 200. In other embodiments, the beam splitter 150 can be a thin film polarizer. This combination 150 can let through the seed pulses from the oscillator 100 to the stretcher-compressor 200, but redirect the stretched pulses coming back from the stretcher-compressor 200 toward the amplifier 300, because the λ/4 plate rotates the polarization plane of the beam of pulses by 90 degrees upon double passing. The polarizer, while transmissive for the polarization direction of the seed pulses, is reflective for the 90 degree rotated polarization plane of the stretched pulses, after they cross the lambda/4 plate the second time.

In some embodiments, the laser engine 1 can include a Faraday isolator 500 in the optical pathway between the beam splitter 150 and the amplifier 300. The functions of the Faraday isolator 500 can include the isolation of the oscillator 100 from the amplified beam in order to prevent damage by the high power of the laser beam to the oscillator 100. Such a Faraday isolator 500 can receive the stretched seed pulses from the beam splitter 150, transmit the stretched seed pulses toward the amplifier 300, receive the laser beam of amplified stretched pulses from the amplifier 300, and output the laser beam of amplified stretched pulses towards the stretcher-compressor 200 through polarizers 550 and 560.

Faraday isolators 500 can be useful in embodiments where the amplifier 300 outputs the amplified pulses through the same optical path it received them, because simple redirecting optics maybe quite inadequate for the isolating function as the amplified pulses often have a power or intensity which is hundreds or even thousands of times greater than that of the seed pulses. Even if the simple redirecting optics lets through only a fraction of these amplified pulses, the transmitted pulses can still be intense enough to damage the oscillator 100.

In some embodiments, the Faraday isolator 500 can be configured to let less than a $\frac{1}{10,000}$ portion of the laser beam from the amplifier 300 through towards the oscillator 100. The same isolating function can be captured in terms of attenuation: the Faraday isolator may attenuate the amplified laser beam by e.g. 40 dB or in some implementations by 50 dB.

The Faraday isolator, or polarization dependent isolator, may include three parts: an input polarizer, polarized vertically, a Faraday rotator, and an output polarizer or analyzer, polarized at 45 degrees.

Light travelling in the forward direction becomes polarized e.g. vertically by the input polarizer, if it wasn't already polarized in that direction. (Here, the polarization plane refers to the plane in which the electrical field vectors lie. Further, "vertical" only establishes a convention or a reference plane. In various embodiments the actual polarization plane can be oriented into other specific directions.) The Faraday rotator rotates the polarization plane of the beam by about 45 degrees, aligning it with the polarization plane of the analyzer, which then transmits the light without additional rotation of the polarization plane.

Light travelling in the backward direction, such as the amplified pulses returning from the amplifier 300, becomes polarized at 45 degrees relative to the reference vertical plane after exiting the analyzer. The Faraday rotator again rotates the polarization by about 45 degrees. Therefore, the light outputted by the Faraday rotator towards the input polarizer is polarized horizontally. Since the input polarizer is vertically polarized, the horizontally polarized light will be reflected by the input polarizer with near perfection instead of transmitting it to the oscillator 100. Thus, the Faraday isolator 500 can protect the oscillator 100 from the high energy amplified laser pulses with a high efficiency.

The Faraday rotator typically achieves its function by generating a magnetic field pointing in the direction of the optical axis. Some Faraday rotators include permanent magnets to achieve this functionality.

The optical materials used in Faraday rotators typically have a high Verdet constant, a low absorption coefficient, low non-linear refractive index and high damage threshold. Also, to prevent self-focusing and other heating-related effects, the optical pathway is typically short. The two most commonly used materials for the 700-1100 nanometer range are terbium doped borosilicate glass and terbium gallium garnet crystal (TGG).

Embodiments of the laser engine 1 or 1' where the amplifier 300 does not output the amplified pulses via the same optical pathway as they entered may not need to employ the Faraday isolator 500.

Figure 4:
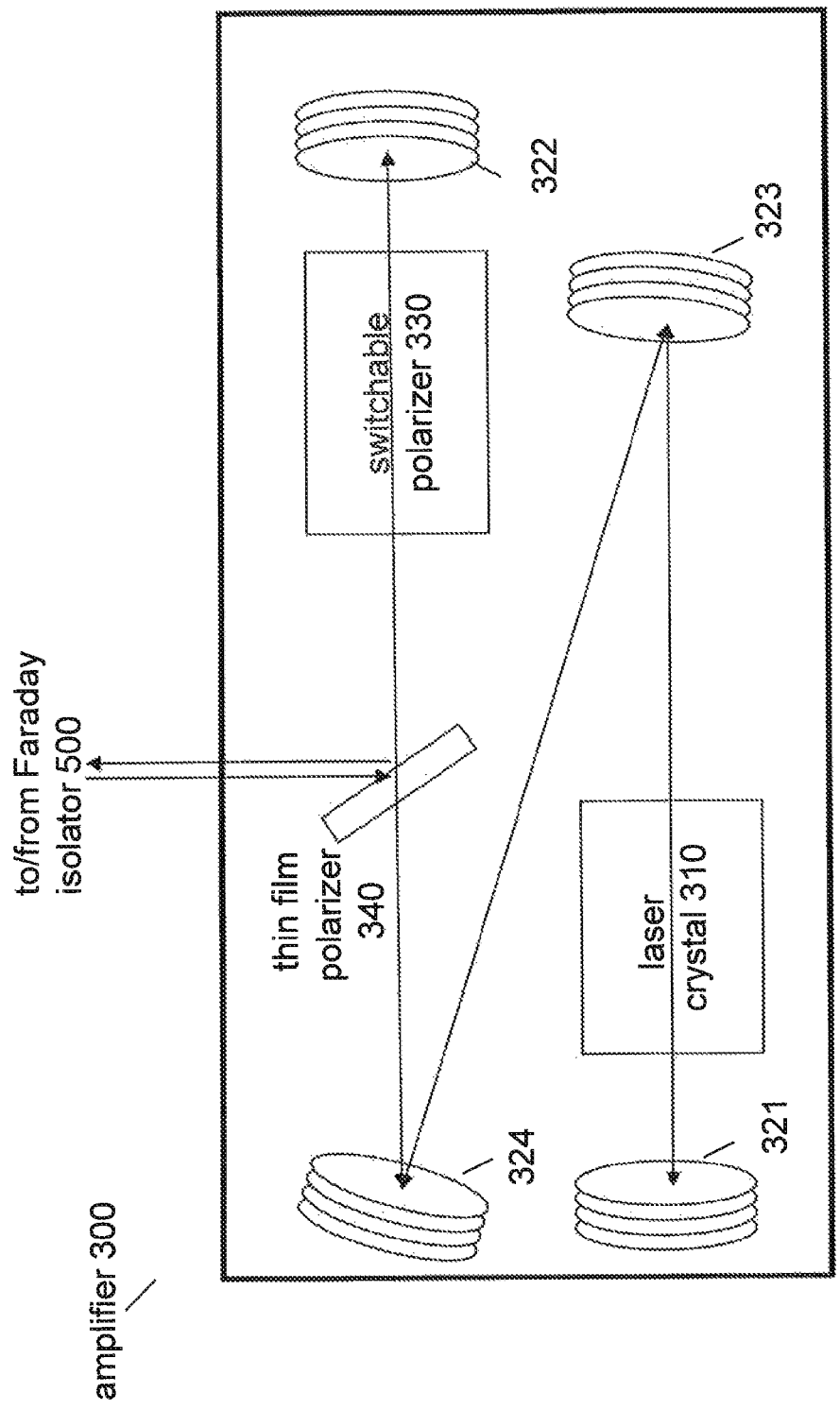
FIG. 4 illustrates an embodiment of an amplifier 300.

FIGS. 2 and 4 illustrate that the light transmitted from the Faraday isolator 500 can enter the amplifier 300. The amplifier 300 can include a laser crystal, or gain medium 310 to amplify the stretched seed pulses which make roundtrips between end-mirrors 321 and 322. Some amplifiers 300 can include a folded optical pathway (or "z-cavity"), redirecting the laser beam with folding mirrors to reduce the spatial extent of the resonant cavity. The amplifier 300 in FIG. 4 has four mirrors: the two end-mirrors 321 and 322, which define the resonant cavity, and two folding mirrors 323 and 324. In some examples, the optical pathway can even fold over itself, appearing as a crossing pattern. While utilizing more folding mirrors can reduce the size of the amplifier 300 even further by folding the optical pathway into a more compact space, the additional mirrors increase the potential for misalignment and the price.

In addition to the laser crystal 310 and mirrors 321-324, the amplifier 300 can include a switchable polarizer 330, which controls the quality factor Q and thus the amplifying function of the amplifier 300, as well as a thin film polarizer 340, which serves as an input/output port for the pulses in the cavity. The thin film polarizer 340 is a specific example of a polarization-selective device which reflects light with a first predetermined polarization, while transmitting light with a second polarization that is orthogonal to the first predetermined polarization. The switchable polarizer 330 can be a polarization device that switches between a first operating state when it does not rotate the polarization of the light passing through it and a second operating state when it rotates the polarization of the light in response to a control signal applied thereto. The combination of the thin film polarizer 340 and the switchable polarizer 330 can be used to control when the pulses coming from the Faraday rotator 500 are coupled into the amplifier 300, and when the pulses amplified inside the amplifier 300 are coupled out from the amplifier, as explained below.

This combination of the thin film polarizer 340 and the switchable polarizer 330 in FIG. 4 is an example of an optical switch for the resonant cavity of the amplifier 300. Other designs can be also used for this optical switch.

The operation and the structure of the amplifier 300 are described in further detail below. In particular, it will be shown that changing the repetition rate is often accompanied by changing the number of roundtrips an amplified pulse makes between the end-mirrors 321 and 322. A function of the just-described optical switch is to control the number of these roundtrips by controlling when pulses are coupled into or out of the resonant cavity.

The optical elements in the amplifier 300 can introduce a certain amount of dispersion during each of these roundtrips. Thus, changing the number of roundtrips in the amplifier 300 in relation to changing the repetition rate changes the cumulative dispersion of the amplified pulses outputted by the amplifier 300. Even if the compressor 400 is adjusted to compensate the dispersion for a particular number of roundtrips, the change of the dispersion from the change of the number of roundtrips upsets the sensitive balance of stretching, dispersive amplification and compression of the stretcher 200', the amplifier 300 and the compressor 400 of the laser engine 1' of FIG. 1B, requiring lengthy recalibration. Even the more inventive architecture of the laser engine 1 with the integrated stretcher-compressor 200 in FIG. 1A may require the use of a compensating element to be adjusted when the number of roundtrips is changed. This aspect limits the utility of these laser engines.

To broaden their utility, some laser engines can include a dispersion controller or compensator as part of the amplifier 300. A function of the dispersion controller is to introduce dispersion opposite and essentially equal to the dispersion introduced by the optical elements of the amplifier 300 during a roundtrip. As a result of this dispersion compensation or control, the pulses acquire little or no dispersion during the roundtrips in the resonant cavity of the amplifier 300. Thus, changing the number of roundtrips changes the dispersion of the amplified pulses only to a miniscule degree or not at all.

Therefore, the repetition rate of the laser pulses can be varied with essentially no adjustment, re-alignment or calibration of the optical setup of the compressor 400 or stretcher-compressor 200 as no dispersion accumulates during the roundtrips to compensate. Accordingly, the dispersion-controlled amplifier 300 can be implemented in the laser engine 1' of FIG. 1B to relieve the compressor 400 from the task of time-consuming realignments upon the change of repetition rates. Moreover, this dispersion-controlled amplifier 300 enables the use of the integrated stretcher-compressor 200 in the laser engine 1 of FIG. 1A without adjustable compensating functionalities.

For example, if the laser crystal 310 introduces a positive dispersion during a roundtrip of a lasing pulse inside the resonant cavity, the dispersion controller can introduce a negative dispersion of the same magnitude to the amplified stretched pulses to suppress, minimize or eliminate the dispersion of the lasing pulse.

A useful measure to quantify the dispersion is the "group delay dispersion", or GDD, often defined as:

$$GDD = \frac{\lambda^3}{c^2} \frac{d^2 n(\lambda)}{d\lambda^2} L \quad (1)$$

where $\lambda$ is the wavelength of the light, c is the speed of light, $n(\lambda)$ is the wavelength dependent index of refraction and L is the length of the optical pathway in the cavity. The GDD of the optical elements 310, 330 and 340, the mirrors 321-324, and any other optical element which may be present in the amplifier 300 can be determined e.g. by measurement or inferred from the design. Armed with the knowledge of the GDD, a dispersion controller can be implemented in the cavity with a GDD of approximately equal and opposite value to the determined GDD of the optical elements of the amplifier 300. The so-designed cavity produces little or no dispersion during the roundtrips of the pulses, eliminating the described problems and broadening the utility of the laser engines 1 or 1'.

In an illustrative example, in a typical CPA laser engine 1' a 500 femtoseconds seed pulse can get stretched by 200 picoseconds to a stretched pulse length 200.5 ps by the stretcher 200'. The corresponding compressor 400 may be adjusted and calibrated to compress the stretched pulse back by 200 ps, resulting in a compressed pulse length of ideally about 500 fs. Accounting for imperfections, in realistic cases the compressed pulse length may fall in the range of 500-800 fs.

However, during the roundtrips of the stretched pulses in the resonant cavity of the amplifier 300, the length of the stretched pulses may get enhanced by the dispersion of the various optical elements of the amplifier 300, represented by the GDD of the cavity. Typical values of the GDD can vary from hundreds of $fs^2$ to hundreds of thousand $fs^2$. In some cases the GDD can be within the range of 5,000 $fs^2$-20,000 $fs^2$. Since typically the stretcher 200 and the compensator 400 cancel each other's effect on the pulse length, the length of the pulse $\Delta t(out)$, outputted by the laser engine 1, is related to the length of the seed pulse $\Delta t(seed)$, generated by the oscillator 100, and the GDD via the following relation:

$$\Delta t(\text{out}) = \frac{\sqrt{\Delta t(\text{seed})^4 + (4\ln 2 N \times GDD)^2}}{\Delta t(\text{seed})} = \Delta t(\text{seed}) \sqrt{1 + 7.69 N^2 \times \left(\frac{GDD}{\Delta t(\text{seed})^2}\right)^2} \quad (2)$$

where N is the number of roundtrips in the cavity.

Thus, for example, the length of a $\Delta t(seed)=200$ fs seed pulse can be increased by as little as 22 fs to $\Delta t(out)=222$ fs during a single roundtrip by the optical elements of the amplifier with a GDD of 7,000 $fs^2$. However, this seemingly small dispersion gets compounded during the repeated roundtrips. After N=10 roundtrips the length of the outputted pulse increases by about 790 fs to $\Delta t(out)=990$ fs, after N=30 roundtrips by about 2,700 fs=2.7 ps to $\Delta t(out)=2,920$ fs=2.9 ps, and after N=100 roundtrips by about 9.5 ps to $\Delta t(out)=9.7$ ps. Visibly, without a dispersion controlled amplifier 300 this substantial deterioration of the pulse length by a factor of up to about 50 transforms the laser from a femtosecond laser to a picosecond laser.

Further, even if the compressor 200 or 400 is calibrated to compensate the additional dispersion caused by a specific number of roundtrips, e.g., the 9.5 ps dispersion corresponding to the N=100 roundtrips, when an application calls for changing the number of roundtrips from N=100 to, e.g., N=110, another 1 ps dispersion is induced by the amplifier 300, again resulting in a compressed pulse length of picoseconds instead of femtoseconds.

In contrast, embodiments of the laser engine 1 or 1' can have a dispersion controller inside the amplifier 300 to compensate the GDD caused by the optical elements of the resonant cavity. This dispersion controller can compensate the few fs per roundtrip dispersion induced by the optical elements in the amplifier. Thus, the amplifier 300 can receive stretched pulses with a 200 ps pulse-length and emit amplified pulses with essentially the same 200 ps pulse-length, approximately independently from the number of roundtrips the amplifier is operated at, let that number be 50, 100, 200 or 500. Therefore, the stretcher-compressor 200 of the laser engine 1, or the compressor 400 of the laser engine 1', can compress the pulse-length back to the femtosecond range for a wide range of the number of roundtrips N and hence for a wide range of repetition rates without necessitating the time-consuming re-adjustment and calibration of other laser systems that lack the present dispersion control or compensation inside the amplifier 300. The dispersion controller inside the amplifier 300 is in the internal optical path of the amplifier 300 and thus automatically compensates the GDD/dispersion without requiring a re-adjustment of the optical elements outside the optical amplifier 300. With the proper design of the dispersion controller inside the amplifier 300, the need for having adjustable dispersion elements outside the optical amplifier, such as the dispersion compensation gratings in FIG. 3B, to be re-adjusted for changing the pulse repetition rate, can be eliminated.

Enabled by the above design considerations, the laser engines 1 or 1' can produce a laser beam with a pulse duration less than 1000 femtoseconds with repetition rates in the 10 kHz-2 MHz range with essentially the same setup of all of the optical elements of the laser engine other than those of the oscillator 100. Other embodiments can operate with a repetition rate in the range of 50 kHz-1 MHz, yet others in the range of 100 kHz-500 kHz.

Therefore, in these laser engines, the repetition rate can be varied from a first value to a second value without changing the setup of the optical elements of the laser engine other than the oscillator 100.

There can be laser engines where the change of the repetition rates from its first value to the second value is accompanied by a change of the setup of the optical elements. However, some of these laser engines may be modifiable based on dispersion compensation or control inside their amplifier so that the modified laser engines can be operated to output the laser beam with the second repetition rate with an unmodified setup as well.

In various implementations of the laser engine 1 the repetition rate can be varied from a first value to a second value, where the second repetition rate is different from the first repetition rate by at least 10%, 50%, 100% or 200%.

In some designs, where the resonant cavity employs optical fibers, an adjustment of the repetition rate may also be possible without retuning and adjusting a subsequent compressor 400. However, these fiber lasers (i) have serious limitations on the energy of the pulses, and (ii) often do not have dispersion controllers. They typically produce pulses only with energy below 10 micro Joule (µJ) per pulse to avoid the danger of damaging the fiber cavity. As described below, for many ophthalmic and surgical applications this energy per pulse may be insufficient, as those applications may require 20 or more µJ/pulse on target, translating to 30 or more µJ/pulse outputted by the laser accounting for the various losses.

Another point of difference is that in fiber lasers the divergence of the beam unavoidably changes when the repetition rate of the laser changes because of the variation of the thermal load.

In contrast, the amplifier 300 typically contains a dispersion controller or compensator and the light propagates in free space so that some examples of the laser engine 1 or 1' can be operated to output a laser beam with an energy in the range of 1-100 µJ/pulse, others with an energy in the range of 10-50 µJ/pulse, yet others with an energy in the range of 20-30 µJ/pulse.

Some laser engines 1 or 1' may be configured so that the changing of the repetition rate is accompanied with an adjustment of an optical element of the laser engine 1. However, because of the presence of the dispersion controller, even in these embodiments the laser engine 1 or 1' may be modifiable to utilize essentially the same setup of the optical elements when the repetition rate is changed.

The above described examples can be implemented in many different ways. In some embodiments the dispersion controller or compensator inside the optical amplifier can include one or more chirped mirrors, chirped fibers, various chirped gratings, chirped transmissive optical elements, prisms, and other optical elements, capable of changing the dispersion of the incident light.

In general, chirped optical elements can have a number of layers with modulated optical properties. In examples, the thickness of the layers and the variation of their refractive index can be designed to control light with different wavelength differently. An example, the chirped volume Bragg grating (CVBG) has been already described in relation to the stretcher-compressor 200. Other examples, such as chirped mirrors can include layers of dielectric materials, where each single dielectric layer, or short stack of layers, can reflect a narrow vicinity of a specific wavelength. The chirped mirror can be constructed by forming a first stack of 5-10 dielectric layers with thickness suitable to reflect light with a wavelength in a vicinity of a first wavelength. Then a second stack of 5-10 dielectric layers can be formed on top of the first stack with a different thickness and/or index of refraction to reflect light with a wavelength in the vicinity of a second wavelength and so on. When formed with a sufficient number of layers in a suitable number of stacks, the chirped mirror can reflect light with wavelength components in a selected band of wavelengths, while transmitting light with other wavelengths.

The dispersion controlling function in the amplifier can be performed by making one or more of the mirrors 321-324 chirped. In FIG. 4 all four mirrors are chirped. Other designs may have only one or two of the mirrors chirped. Yet others may employ one or more chirped optical element. As possible realizations of the dispersion controller, these one or more chirped mirrors can control, compensate, minimize, or even eliminate the dispersion, induced by the optical elements 310, 330 and 340 and the mirrors 321-324 during a roundtrip of an amplified stretched laser pulses inside the resonant cavity of the amplifier 300.

The laser crystal 310 can be Nd or Yb based. Examples include Nd:YAG and Yb:YAG crystals. Other implementations may use Nd or Yb doped glass. Yet others Yb:tungstates of the form Yb:X(WO$_4$)$_2$ or Yb:sesquioxides of the form Yb:X$_2$O$_3$. In these cases, X can be Y, Lu, Gd or other suitable elements. The Nd or Yb doping level can be in the range of 0.1-100%.

The spatial doping profile of the laser crystal may be chosen to ensure the emission of high quality single mode laser pulses. Some doping profiles may be compatible with a pumping light source with limited focusability as expressed by a larger than usual M$^2$ factor of the pumping light. The pumping source can be in a side-pumping or in an end-pumping arrangement. The pumping light source may contain multiple fiber-coupled diodes, such as 2-10 diodes, each emitting with 1-10 W of power. The pumping diodes can operate in an essentially continuous wave (CW) operation mode, or in an analogous high frequency pulse mode. They can be arranged in different spatial arrays, bars or other forms. The light from the diodes can be guided through a shared grating, which may return a very small percent of the light to the diodes, thus phase locking their light.

FIGS. 5A-B, in combination with FIG. 4, illustrate the operation of the cavity dumped regenerative amplifier CDRA 300. The principle of the operation is often referred to as "Q-switching", referring to the switching of the quality factor Q of the resonant cavity.

In a "recharge", or "pump" phase, the thin film polarizer 340 reflects the incoming light through the switchable polarizer 330. The switchable polarizer 330 can be a shutter, a chopper wheel, a spinning prism or mirror, an acusto-optic device, an electro-optic device, such as a Pockels cell or Kerr cell, or a switchable µ/4 wave-plate. In an unbiased or low voltage state the switchable polarizer 330 can rotate the polarization plane by 90 degrees as the pulses pass through twice, to and from the end-mirror 322.

During the recharge or pump period the Faraday isolator 500 transmits pulses onto the thin film polarizer 340 which redirects them through the switchable polarizer 330. Returning from the end-mirror 322 the pulses cross the switchable polarizer 330 for the second time. Then they perform one roundtrip in the cavity, passing through the switchable polarizer 330 two more times on their way to and from the end-mirror 322. After one roundtrip these four passes through the switchable polarizer 330 rotate the polarization plane of the pulses by 180 degrees. Thus, they get reflected out of the cavity by the thin film polarizer 340 essentially without amplification.

In this same recharge or pump period the amplifier 300 suppresses the lasing action of the light generated by the pumping diodes inside the cavity as well, as the 90 degree double pass rotation of the polarization plane by the switchable polarizer 330 makes the quality factor Q of the resonant cavity low, making the cavity unsuitable for lasing action.

FIG. 5A illustrates that in this recharge/pump phase the laser crystal 310 absorbs the light from the above described pump diodes, or pump laser diodes, in a side- or end-pumping arrangement. The pumping increases the population of an excited energy level of the lasing atoms or complexes to create population-inversion, in essence absorbing and storing the pumping energy or "gain".

FIG. 5B illustrates that in this recharge/pump phase no amplified laser pulses are generated in and emitted by the amplifier 300. The rejected unamplified pulses, of course, are emitted by the amplifier 300.

FIGS. 5A-B illustrate that the pump/recharge phase can end either according to a predetermined timing operation or prompted by a sensing electronics which tracks the energy storage in the laser crystal 310. In either case, after a time t(recharge) a control and driver electronics may apply a high voltage to the switchable polarizer 330 to stop rotating the polarization plane by 90 degrees. Other types of the switchable polarizer 330 may be switched by different means. This change switches the quality factor Q of the cavity to a sufficiently high value to make the cavity suitable for lasing action.

Single pulse embodiments of the amplifier 300 can switch the switchable polarizer 300 while a single pulse is performing its roundtrip inside the cavity. When at the end of its roundtrip the single pulse returns to the switchable polarizer 300 after that has switched, the polarization plane of the pulse is not rotated anymore and therefore the pulse is not reflected out from the cavity by the thin film polarizer 340. Instead of getting rejected as during the pump phase, the pulse can be trapped in the cavity for several more roundtrips for a gain period of length t(gain). In FIG. 5B the time scale of t(gain) has been magnified for clarity.

FIGS. 5A-B illustrate that in the gain period the energy (or gain) pumped and stored in the cavity gets transferred from the laser crystal 310 to the pulse making the roundtrips, via the process called induced emission to start the lasing action. Accordingly, the energy in the cavity decreases, as shown in FIG. 5A, whereas the energy in the lasing pulse builds up in a gain process, as shown in FIG. 5B. In FIG. 5B the peaks in the t(gain) interval represent the energy of the lasing pulse as it passes a particular point in the cavity, whereas the solid rising curve is an envelope representing the energy gain averaged over a sliding roundtrip period.

It is noted that implementations which trap a single incoming pulse in the cavity can transfer just about all of the energy stored in the laser crystal 310 into the single lasing pulse during its roundtrips. In contrast, some implementations may allow multiple pulses into the cavity. However, in these examples the resulting laser beam may have a lower energy per pulse thus reducing the energy per pulse below levels which are customary and beneficial for the relevant type of photodisruption.

After the energy pumped into the cavity is transferred to the lasing pulse with a high efficiency during a sufficient number of roundtrips, the controller-driver electronics may stop applying the high voltage to the switchable polarizer 330, causing it to resume rotating the polarization plane of the lasing pulse. Because of the restart of the polarization rotation, the amplified laser pulse is then reflected out from the cavity by the thin film polarizer 340 at the end of the next roundtrip, at a time denoted t(dump).

The dumping of the amplified laser pulses can be controlled in different ways. In some cases design calculations and computer methods can be relied upon to set the number of roundtrips after which the dumping is performed. In others, prior calibration can be used to set the number of roundtrips. In yet other cases, a wide variety of sensors can be coupled into the optical path of the resonant cavity. This sensor or sensors can sense when the energy of the amplified lasing pulses reaches a predetermined value and send a control signal to a controller to dump the cavity accordingly.

Reflecting the amplified laser pulse out from the cavity and transmitting it towards the compressor 400 completes the pump-gain-dump cycle. Once the pulse-dumping is complete, the cavity returns to its low Q state, restarting the pump-gain-dump cycle anew. In some designs, the pulse-injection port and the pulse-dumping port may be different. In FIG. 4 both of these ports are implemented in the thin film polarizer 340.

In some implementations the lasing pulses perform 50-500 roundtrips, in other examples 100-200 roundtrips inside the cavity to enable the transfer of energy from the pumped state of the laser crystal 310 to the lasing pulse. As discussed before, the oscillator 100 can create a seed pulse train with a frequency in the range of 10-200 MHz, in some cases in the range of 20-50 MHz. In some implementations, the laser engine 1 or 1' outputs a laser pulse train with a repetition rate in the ranges of 10 kHz-2 MHz, or 50 kHz-1 MHz, or 100 kHz-500 kHz. Thus, the switchable polarizer 330 decimates the incoming seed pulse train by trapping only every $5^{th}$-20, $000^{th}$ seed pulse for amplification. The timing of these trapping sequences can be controlled by using the oscillator 100 as a master-clock.

The repetition rate is a central characteristic of a laser engine. A larger variety of functionalities can be achieved if (1) the repetition rate can be varied in a range of frequencies, and (2) the top of the range is high. For example, a cataract procedure may be optimally performed at a first repetition rate while a second repetition rate may be better for a corneal procedure. A single laser engine can be used for both of these functionalities if the laser engine can be adjusted to operate both at the first and at the second repetition rate. Therefore, various design considerations will be reviewed next which can make the repetition rate variable and the upper limit of the range high in the laser engines 1 and 1'.

As described in relation to FIGS. 3B-C and FIG. 4, the use of a dispersion controller in the amplifier 300, such as a chirped mirror for any one of the mirrors 321-324, may compensate the dispersion of the lasing pulse caused by optical elements of the amplifier during a roundtrip in the cavity. This design feature allows the changing of the repetition rate of the laser engine 1 or 1' without changing the calibration, alignment or setup of the optical elements of the stretcher 200 and compressor 200/400, such as the gratings 201, 203, 205, and 207, the lens 202 and the mirrors 204 and 208.

Instead of modifying the optical setup, the repetition rate change can be achieved by applying electric control signals to modify the timing and operation of the laser engine 1. For example, the repetition rate can be increased by applying control signals to reduce the repetition time t(rep)=t(recharge/pump)+t(gain).

Typically, the reduction of t(rep) is achieved by reducing both t(pump) and t(gain). The pumping time t(pump) can be shortened e.g. by increasing the pumping intensity of the pumping diodes/lasers. The gain time t(gain) can be shortened e.g. by reducing the number of roundtrips of the lasing pulse.

The energy of the laser pulse can be preserved in spite of the fewer roundtrips e.g. by increasing the energy gain per roundtrip. FIG. 5B illustrates the increase of the energy of the lasing pulse during the gain period as it passes a selected reference point in the cavity roundtrip by roundtrip. The ratio of the energies in subsequent passes is often characterized by the ("small signal") gain factor g. The gain factor g is sensitive to the total energy stored in the excited or pumped level of the laser crystal 310. The more energy stored, the higher the g factor. Therefore, applying control signals to increase the energy stored in the pumped level of the gain medium 310 can make the lasing pulse reach the same energy in fewer roundtrips, thus increasing the repetition rate.

The upper limit of the repetition rate range can be increased in a variety of ways as well. In embodiments with a larger gain factor g fewer roundtrips are needed to achieve the same amplification. Thus, some implementations achieve a high upper limit of the repetition rate by employing a laser crystal 310 which has a higher gain factor g.

Also, since the gain factor g is sensitive to the total energy stored in the excited or pumped level of the laser crystal 310, pumping the excited level with more energy is another way to achieve a shorter t(gain) and thus a higher repetition rate.

Another factor controlling the repetition rate is the time one roundtrip requires. The lasing pulse passes by a reference point at time intervals 2L/c where L is the length of the optical pathway in the cavity and c is the speed of light. Thus, in some embodiments the length L of the optical pathway can be reduced to reduce the time of a roundtrip. In these implementations the same number of roundtrips and thus the transfer of the same amount of energy takes a shorter time t(gain), increasing the repetition rate in yet another way.

Implementing one or more of the above discussed design principles, embodiments of the laser engine 1 or 1' can operate with a repetition rate up to 500 kHz, 1 MHz, or in some cases 2 MHz.

Additionally, in these implementations the reduction of t(gain) allows the use of a larger portion of the total repetition time t(rep) for supporting a more favorable duty for the pump and dump cycle.

An often-used definition of the duty is the length of the low Q period divided by the length of the total period. Using this definition, in an implementation with e.g. a 400 kHz repetition rate, reducing t(gain) from 1 µsec to 0.5 µsec increases the duty from 0.6 to 0.75, a sizeable increase of 25%.

Returning to the design principle of shortening the length L of the optical pathway, it is noted that L is controlled, among others, by how fast the switchable polarizer 330 can switch to trap a pulse in the cavity. In a 1 meter optical pathway cavity the time of a roundtrip is 2L/c=6.6 ns. Accounting for the finite spatial extent of the pulse as well, single pulse implementations therefore have a switchable polarizer 330 with a switching time below 5 ns, others below 4 ns, or even below 3 ns.

In some amplifiers the switchable polarizer 330 can be a Pockels cell. Pockels cells often apply a strong electric field to rotate the polarization of incident light beams. The rotation of the polarization is proportional to the first power of the electric field and thus can be quite strong. The Pockels effect occurs in crystals that lack inversion symmetry, such as lithium niobate or gallium arsenide and other noncentrosymmetric materials.

By sometimes applying kilovolts of voltage, Pockels cells can be switched from a polarization-rotating state to a polarization-non-rotating state with a very short rise time. One measure of the rise time is the "5-95 time", the time it takes for the rotation of the polarization plane to rise from 5% of the maximum/saturation value to 95% of it. In some implementations the rise time can be less than 5 ns, in others less than 4 ns, in yet others, less than 3 ns. In fact, in some implementations, the rise time is limited not by the dynamics of the Pockels cell itself, but rather by that of the switching electronics. Some implementations may use an innovative control and driver circuit to enable this fast power switching process.

As described above, the shortening of the switching time of the Pockels cell is an effective way to shorten t(gain), enabling a faster repetition rate. Furthermore, these faster Pockels cells also allow the reduction of the length of the optical pathway and thus the size of the cavity.

Further, implementations of the laser engine 1 can be made to have fewer optical elements than some existing lasers. This is due in part to the application of the dispersion controller or compensator, obviating the need for adjustable optical elements in the compressor, as well as to the integrated stretcher-compressor architecture 200.

While some lasers may contain hundred or more optical elements, in some implementations of the laser engine 1 the number of optical elements may be less than 75. In others, less than 50.

In some implementations the number of optical elements in portions other than the oscillator can be less than 50. In others, less than 35.

Here the term "optical element" refers to any element which impacts an optical property of a light beam. Examples include: a mirror, a lens, a parallel plate, a polarizer, an isolator, any switchable optical element, a refractive element, a transmissive element, and a reflective element.

Optical elements are defined by surfaces where the light enters from the air and exits into the air. Therefore, a functional block, such as an objective, is not one "optical element" if it contains several lenses, even if the lenses rigidly move together when the objective is moving. This is so because between the lenses of the objective the light does propagate in air, however short is the separation. Even if two lenses touch each other without an airgap at their center, off-center beams still exit one lens into the air before entering the other one, and thus are counted as two optical elements. It is noted that schematic descriptions of lasers often show fewer optical elements than what is necessary for the actual functioning of the laser. Typically, when a single lens is shown, its functionalities cannot be performed by an actual single lens, only by a carefully designed lens-assembly. Thus, such schematic descriptions are typically meant to be illustrative only and would be inoperable if implemented literally.

Implementations of the laser engine 1 with fast Pockels cells, fast switching electronics and a small number of optical elements can have an optical pathway inside the cavity shorter than 2 meters, others shorter than 1 meter. Correspondingly, the total optical pathway of the laser engine from the generation of the photons in the oscillator 100 and including all the roundtrips inside the cavity of the amplifier 300 can be less than 500 meters, or 300 meters, or even 150 meters.

Existing femtosecond lasers have a total optical pathway of 500 meters or longer and a cavity end-mirror-to-end-mirror distance of 3-4 meters or longer because it is prohibitively difficult to shorten the optical pathway below these values without the here-described innovative solutions.

The list of innovative subsystems and features which can contribute to the reduction of the size of laser engine 1 includes: (i) a fiber-based oscillator 100 instead of a free-space oscillator; (ii) an integrated stretcher-compressor 200, possibly based on a single Chirped Volume Bragg Grating, which does not have optical elements to be adjusted when the repetition rate is changed; (iii) a dispersion-compensated amplifier 300, eliminating the need for adjustable optical elements in the stretcher-compressor 200 when changing the repetition rate; (iv) an unusually fast-switching Pockels cell; (v) an unusually fast control electronics which can operate with fast rise times at the high voltages of the Pockels cell including the kilovolt range; and (vi) a small number of optical elements, requiring less space for accommodation.

Laser engines which implement a combination or all of these features can support an overall free-space optical path length of less than 500 meters, in some implementations less than 300 meters and in some less than 150 meters.

Also, the amplifier 300 with some or all of the above relevant features can have an end-mirror-to-end-mirror optical pathway length of less than 2 meters, in some cases less than 1 meter.

In many implementations the optical pathway is multiply folded, thus the physical extent of the resonant cavity can be considerably shorter than the length of the pathway. Short and folded optical pathways can translate into a small overall extent of the amplifier 300. In some cases, none of the edge sizes of the amplifier 300 exceeds 1 meter, in other cases, 0.5 meter.

Correspondingly, the footprint of the entire laser engine 1, i.e. the area it covers on the deck of a laser system, may be less than 1 $m^2$, in others 0.5 $m^2$, in yet others 0.25 $m^2$, and possibly less than 0.1 $m^2$. Each of these areas or footprints can lead to distinctly new advantages.

The amplifier 300 and the laser engine 1 can have this unusually small spatial extent because of using one or more of the above described design principles and components. As such, the spatial extent can legitimately distinguish the amplifier 300 and the laser engine 1 from other lasers which do not employ these design principles and components.

Another consideration also deserves mention: it is critically simpler to service subsystems which are on the top deck of a laser system and are thus accessible by simply removing a cover but without moving system blocks in and out from the chassis of the laser system. Doing so can endanger the sensitive alignments of the system blocks in a customer environment (such as a hospital), where precision equipment is typically not available to restore the alignment. Thus, while stacking the various components of a surgical laser system, on top of each other may seem as another way to reduce its footprint, doing so would introduce prohibitive challenges for the service of the laser system.

Therefore, reducing the size of the laser engine 1 allows the placement of other subsystems on the top deck of the laser system which also require access for maintenance. Such additional subsystems may introduce qualitatively new functionalities, thus critically improving the utility of the overall laser system. Such additional subsystems can include an imaging system to guide an ophthalmic surgery.

To summarize, the above features, alone or in combination, can be implemented to construct physically compact laser systems. Such a small spatial extent can be a valuable asset for at least the following reasons: (i) ophthalmic surgical laser systems are often deployed in very crowded operating theatres where space and access is at a high premium, favoring laser systems with small footprints; (ii) the serviceability of the laser engine is qualitatively better if most or all of its optical components fit on the top deck of the chassis of the laser system; and (iii) small laser engines allow the deployment of additional systems on the top deck, adding critical new functionalities to the overall laser system, such as imaging systems to guide the ophthalmic surgery.

Returning to tracking the path of the amplified stretched laser pulses, FIG. 2 illustrates that, once emitted by the amplifier 300, the amplified pulse can be forwarded back to the Faraday isolator 500. One of the functions of the Faraday isolator 500 can be to redirect the amplified pulses away from the oscillator with near-100% efficiency, thus preventing damage to the oscillator 100 by the amplified pulse.

In some cases the amplified pulses are directed to a compressor port of the stretcher-compressor 200 via polarizers 550 and 560. As described above, the stretcher-compressor 200 can re-compress the amplified pulses and emit a pulsed laser beam with femtosecond pulses.

Implementations of the laser engine 1 utilizing the various solutions described above can output a laser beam with pulse duration in the range of 1-1000 femtoseconds (fs), in some cases 50-500 fs, in yet others 100-300 fs. These femtosecond pulses can reach unusually high energies, e.g. energies in the range of 1-100 µJoule/pulse, in others 10-50 µJoule/pulse, in yet others 20-30 µJoule/pulse.

These pulse energies can enable useful applications which are not accessible for lasers whose pulse energy is less than 1, 10 or 20 µJoule/pulse, because there are several different laser-tissue interactions in the eye which exhibit a threshold behavior. There are surgical procedures where laser pulses below 1 µJoule/pulse energies do not cause the surgically desired tissue modification. In other surgical procedures this threshold can be 10, or 20 µJoule/pulse.

For example, cataract surgery requires directing the laser deep in the target tissue, such as to a depth of 10 mm. This requirement constrains the numerical aperture, thus calling out for higher energy per pulse values to produce photodisruption. In some cases 10-15 µJoule/pulse energies can be sufficient. To avoid operating at the maximum energy values, devices with 20 µJoule/pulse can be desirable. As these numbers are on-target energies, to account for losses along the optical path, the laser system may include lasers which output 25-30 µJoule/pulse.

For example, in a cataract surgical application, cutting cataracts of hardness 1, 2, 3, or 4 may necessitate laser pulse energies above corresponding thresholds. For example, under certain circumstances lasers with pulse energies higher than 10-15 µJoule/pulse can cut cataracts of hardness 1, pulse energies higher than 10-20 µJoule/pulse can cut cataracts of hardness 2, pulse energies higher than 20 µJoule/pulse can cut cataracts of hardness 3 and pulse energies higher than 30-50 µJoule/pulse can cut cataracts of hardness 4. These threshold energies can be impacted by several factors, including the pulse length, the repetition rate, the location of the laser spot within the overall target region, and the age of the patient.

The effect of the laser pulses is a highly non-linear function of its parameters in wide classes of target tissues. Therefore, lasers with the same energy/pulse but different pulse duration may reach different results in the surgical targets. For example, picosecond pulses with a specific energy/pulse value may generate bubbles in ophthalmic tissue which expand uncontrollably, whereas femtosecond pulses with a similar energy/pulse may create bubbles which remain controlled. Accordingly, the above described energy/pulse values can be generated by laser engines emitting femtosecond pulses, i.e. pulses with a length of less than a picosecond.

The strength of the laser beam can be quantified in terms of its power as well. E.g. a 20 µJoule/pulse laser with a 50 kHz repetition rate carries 1 W power. Expressed in terms of power, the above described threshold values can translate to threshold powers of 0.1 W, 1 W, and 10 W at corresponding repetition rates. Thus, laser engines capable of emitting laser beams with a power in excess of these thresholds offer different functionalities.

For example, the Food and Drug Administration classifies medical lasers by their power. The laser class 3B is often used for ophthalmic procedures as its effects have been widely studied. Lasers which output beams with a power less than 0.5 W of power belong to the class 3B. Therefore, lasers with a power less than 0.5 W offer substantially different applications than lasers with a higher power.

FIGS. 6A-D illustrate a functionality of the laser engine 1, taking advantage of its capability of changing the repetition rate at a high speed. In various applications the surgical laser beam causes photodisruption at a focus point, wherein the disrupted region eventually expands into a bubble. As the focal spot is scanned by a scanning optics of the laser system at a scanning speed, a string of bubbles gets generated. These strings of bubbles can form lines or surfaces in a controllable manner. The large number of bubbles reduces the mechanical integrity of the target tissue along these lines or surfaces, making it possible to easily separate the target tissue along the lines or surfaces. In effect, the scanned laser beam "cuts" the target tissue along these lines or surfaces.

In some representative cases the bubbles may be a few microns (p) in diameter, separated by distances of the order of 10-50µ, or more. The surgical laser system typically creates a bubble once every repetition time, the inverse of the repetition rate. Therefore, the bubbles are essentially equally spaced as long as the scanning speed of the laser system is constant.

Bubbles expand after they have been created by the laser pulse. Under various circumstances this expansion can become uncontrolled. Such an uncontrolled bubble expansion can strongly scatter the subsequent laser pulses in the target region, seriously undermining the precision and control of the ophthalmic surgery. Forming the bubbles too close to each other is one of the triggers of such an uncontrolled expansion, as it can cause the bubbles to coalesce. Other possible processes involve the expansion of a bubble can interfere with the formation of the subsequently formed bubbles, causing a cross-talk between them, once again leading to the uncontrolled expansion of the bubbles. Therefore, maintaining a predetermined bubble separation during scanning can be a high priority to retain control over the bubble expansion for ophthalmic surgical laser systems.

However, the scanning of the focal spot typically involves moving parts such as mirrors and galvos. Given the extremely short repetition times, even the smallest inertia and mechanical delay of these moving parts can impact the bubble densities. For example, when scanning along some surgical patterns, the scanning speed may slow down at turning points and corners, possibly leading to an increased density of laser spots and the bubbles. In other cases, simply the geometry of the surgical pattern leads to an enhanced areal density of the bubbles even if the linear bubble density is kept constant.

Figure 6C:
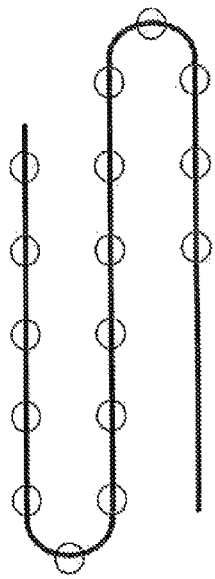
FIGS. 6A-D illustrate scanning surgical patterns with constant and variable repetition rates.
Figure 6D:
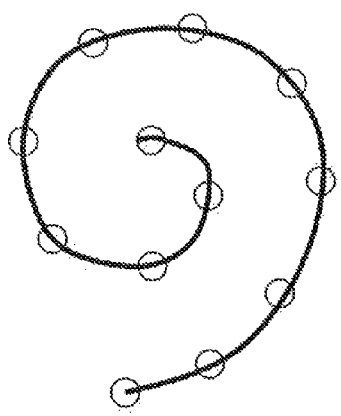
Figure 6A:
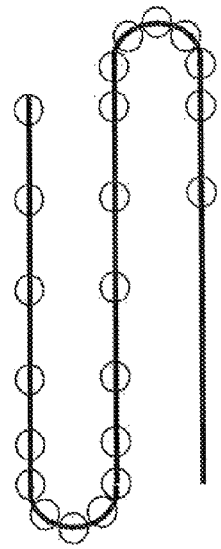

FIG. 6A shows the example when a fixed repetition rate laser is scanning through a switchback surgical scanning pattern in order to create a separation sheet in the target tissue. However, approaching the turnaround or switchback points, the scanner slows down while the repetition rate remains constant and thus creates an increased linear and thus aerial bubble density, as shown. Such an increased bubble density can lead to serious control problems, as described above.

This technical issue is addressed in some existing laser systems by including additional elements, such as a beam blocker, which interrupts the laser beam upon approaching such turning points to prevent the formation of high bubble-density regions. However, including such beam blockers means adding additional elements in the laser system, whose operation is to be controlled and synchronized with the scanning itself. All of these additions mean further challenges and increased complexity.

Similar problems arise even when the scanning simply comes to the end of a line in a scanning pattern, again slowing down of the scanning speed and causing an increased linear bubble density.

Figure 6B:
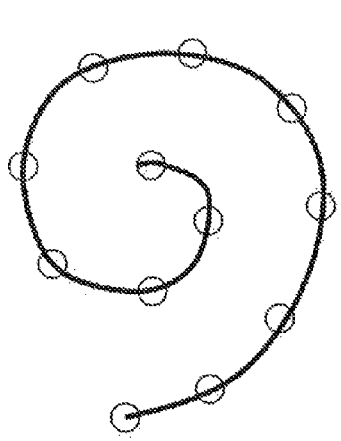

FIG. 6B shows that such sharp turnaround points can be avoided by following "acceleration-minimizing" scanning patterns. An example of an acceleration-minimizing pattern is a spiral, which has no sharp switchbacks. However, even a spiral pattern only decreases the acceleration but does not eliminate it. Therefore, the scanning speed still varies in these systems and thus the fixed repetition rate still has to be selected so that the bubble density does not increase above a threshold value even at the lowest speed sections of the pattern. This design principle, however, means that for most of the pattern the scanning speed is lower than the system could support in order to achieve the bubble density necessary to achieve the cutting or separating function. Equivalently, if a higher scanning speed is utilized then the separation of the bubbles may get smaller, leading to an interference or cross-talk between the forming bubbles. All of these effects increase the danger of uncontrollable or non-deterministic bubble expansion.

Implementations of the laser engine 1 can be designed to offer a useful functionality in this context. The unique design in general and the dispersion controller of the amplifier 300 in particular makes it possible to change the repetition rate essentially synchronously with the changing scanning speed. In some laser engines the repetition rate can be changed in a change-time within the range of 10 µs-1 s, in some special cases in the range of 1 µs-1 s. Therefore, some implementations can include control electronics to slow down the repetition rate of the laser engine 1 according to a designed or measured slowdown of the scanning speed along the surgical pattern to maintain a near constant bubble density in the target region. Such approximately constant bubble density can be achieved, for example, by changing the repetition rate proportionally with the varying scanning speed. With this functionality the laser engines 1 or 1' may be able to form bubbles with a near even linear or areal bubble density or separation and thus prevent or counteract an uncontrolled bubble expansion.

FIG. 6C illustrates a scanning surgical pattern with the same switchbacks as in FIG. 6A, where the repetition rate is reduced as the scan moves around the switchback, generating a cut with an essentially even linear separation between the bubbles.

FIG. 6D illustrates a spiral surgical pattern with a reduced repetition rate as the spiral converges to the center, where bubbles would have been too close to each other without this reduction. This embodiment is therefore once again capable of creating an essentially even areal bubble density.

Of course, the rapid variability of the repetition rate also allows the creation of bubbles not only with a constant density, but with a predetermined density profile as well. For example, the nucleus of the eye is harder towards its center. Therefore, in some implementations, the bubble density may be increased as the scan crosses the center of the nucleus, followed by a decrease past the center. A large number of different density profiles can have different medical advantages and benefits. The density profile can be also adjusted not on a predetermined basis but in response to an imaging or sensing of the target region.

FIGS. 7A-D illustrate yet another design feature helping laser engines to change the repetition rate essentially synchronously with the scanning, or at least within the times scales of the ophthalmic surgery, e.g. within 60-120 seconds.

FIGS. 7A-B illustrate the phenomenon called thermal lensing and its impact on laser design. When the laser crystal 310 is pumped by the pump diodes and then transfers its energy by amplifying the laser pulse, its temperature T rises. The temperature T often rises unevenly: typically the temperature is highest in the pumped center region, possibly peaking at or around the optical axis, and decreases with increasing radial distance.

There are at least two effects of this uneven temperature rise: (i) since the index of refraction n increases with the temperature: $n=n(T)$, it exhibits a maximum in the center region of the laser crystal 310; and (ii) the increasing temperature makes the center region of the laser crystal 310 thermally expand more extensively than its surrounding region and therefore bulge, held by the colder outer region. Both of these effects tend to focus the incident parallel rays. This phenomenon is called thermal lensing. This thermal lensing is referred to by symbolizing the laser crystal with a lens 310'. The thermal lens can exhibit refraction by several diopters and thus it can alter the performance of the laser engine substantially.

FIG. 7A illustrates that the design of a laser engine typically involves determining the refractive effects of the thermal lensing by the laser crystal at the operating temperature T=Top, determined by the operating repetition rate and beam power, and introducing refractive compensation for the thermal lensing via other optical elements of the laser engine. An example is to introduce an additional lens 312, which can restore the convergent beam to a parallel beam after it was focused by the thermal lens 310'.

FIG. 7B illustrates that such a refractive compensation is appropriate for a particular operating temperature T=Top and thus for a particular repetition rate and beam power only. Indeed, if an application calls for a change of the repetition rate or power, the changed repetition rate and/or the changed power changes the temperature T of the laser crystal 310 from T=Top to T=Top'. This change in temperature changes the focusing by the thermal lens with it (from the convergent beam represented by the dotted lines to the one with solid lines), transforming the beam which was parallel at T=Top to diverge at T=Top', thus having poorer convergence properties.

FIG. 7B also illustrates that the convergence properties can be restored by adjusting the refractive compensation. Changing the refractive compensation typically requires adjusting one or more optical element of the laser engine, such as moving a lens, rotating a grating, or moving the beam relative to the optical axis. FIG. 7B shows an adjustment of the compensating lens 312 along the optical axis, as indicated by the arrow. Analogously to the previously dispersion compensation, this refractive compensation via mechanical adjustments is also slow and requires fine tuning and calibration. Therefore, most lasers sidestep this challenge entirely and do not allow for the changing of the repetition rate. And even in those lasers which offer a changeable repetition rate, the rate cannot be changed near synchronously with the scanning of the laser engines, not even within ophthalmic surgical times because the slowness of the adjustment of the compensating optical elements.

Figure 7C:
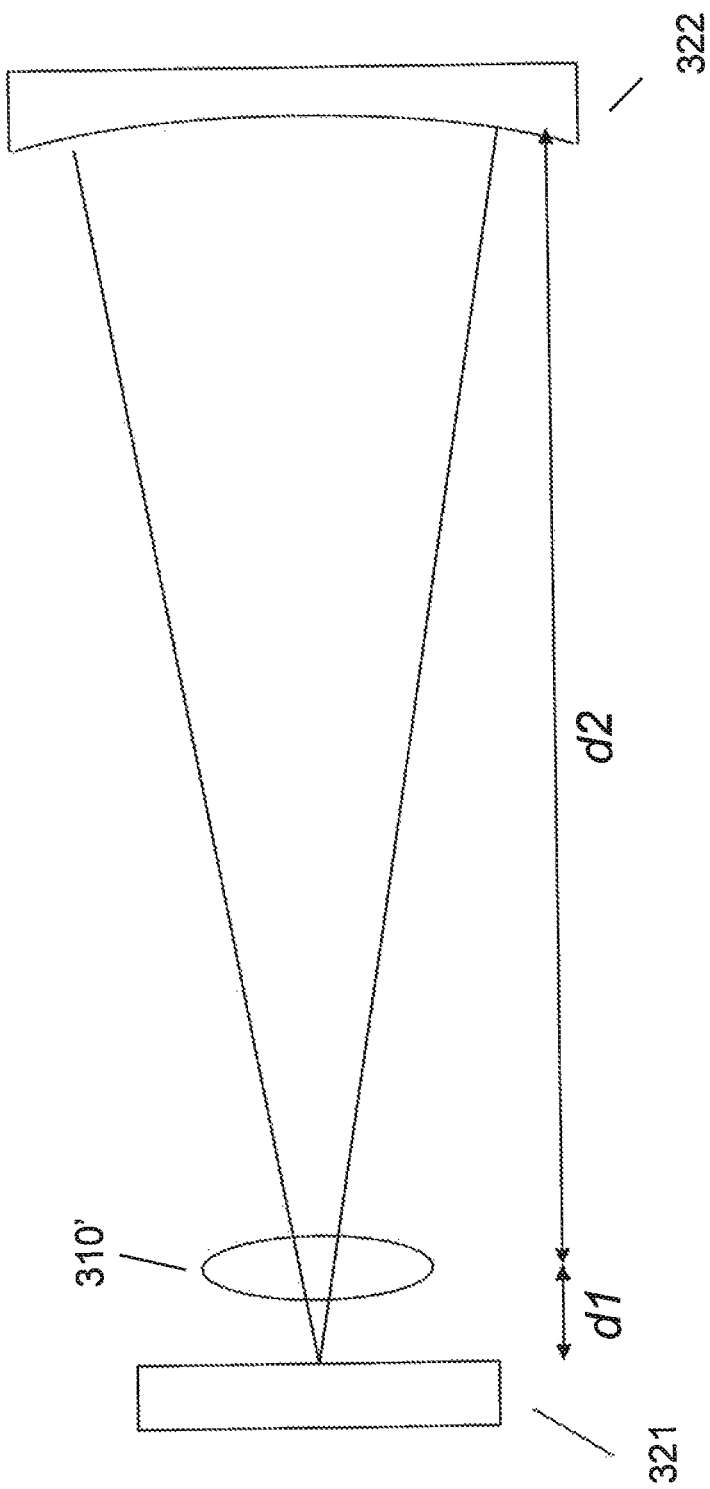
FIGS. 7C-D illustrate two implementations of the amplifier 300 with reduced thermal lensing.
Figure 7D:
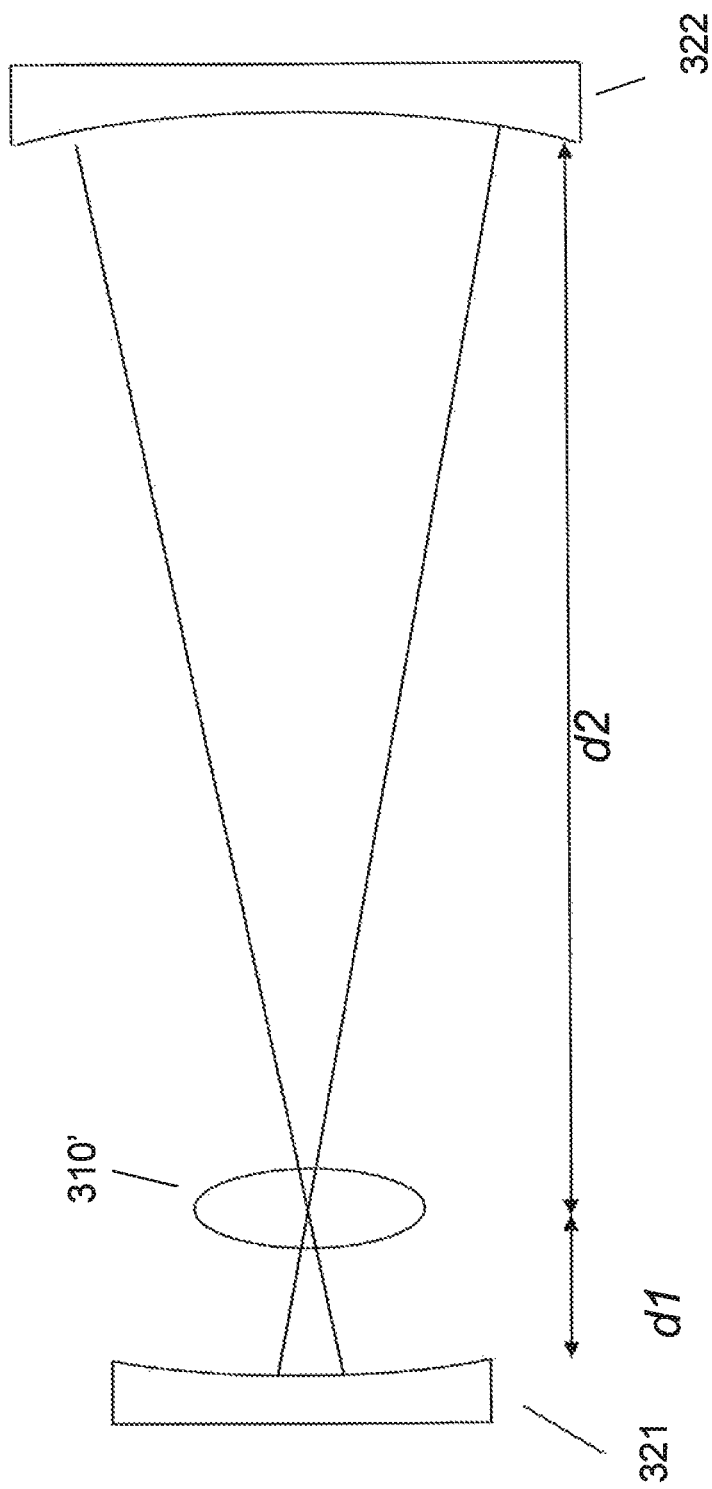

FIGS. 7C-D illustrate implementations of the laser engine 1 employing various design principles to minimize the effect of thermal lensing. The refraction by the thermal lens 310' can be reduced by a considerable degree if most or all the rays propagate through or very close to the center of the thermal lens 310', because rays crossing a lens at its center do not get refracted on the level of the geometrical optics approximation. On the level of wave optics and when including the finite extent of the lens, these central rays do get refracted, but only to a minimal degree.

FIG. 7C illustrates that the rays can be compressed to hit the center of the lens e.g. by (i) using an embodiment of the end-mirror 322 which has a focusing effect; (ii) placing the thermal lensing laser crystal 310/310' very close to the focal point of the focusing end-mirror 322 so that most of the rays from the focusing end-mirror 322 hit the center of the thermal lensing laser crystal 310/310'; and (iii) placing the other end-mirror 321 also very close to the focal point of the focusing end-mirror 322 and thus to the lensing crystal 310 to ensure that the beam reflects back into itself instead of becoming divergent. In such designs, when the repetition rate, or the power of the beam is changed, thus changing the temperature of the laser crystal 310 from T=Top to T=Top', there is no pressing need to readjust any mechanical or optical element of the laser engine 1, since the refractive impact of the laser crystal 310 has been minimized. Thus, the repetition rate, or the power of the beam, can be changed without any corresponding adjustment of a refractive compensator.

Referring to FIG. 4, in various embodiments any one or more of the end-mirrors and folding-mirrors 321-324 can have the described focusing effect.

The designs parameters of this embodiment, including d1, the distance of the end-mirror 321 and the lensing crystal 310, d2, the distance of the lensing crystal 310 and the focusing end-mirror 322, and other parameters, such as apertures, thickness of the lensing crystal 310, and radii of the focusing end-mirror 322, can be optimized to further minimize the already reduced thermal lensing.

FIG. 7D illustrates a related design. In this embodiment both end-mirrors 321 and 322 are of the focusing type. This example further reduces the thermal lensing as the laser crystal 310 can be placed into the shared focal point of the two end-mirrors with higher precision. Again, the other parameters can be made subject to an additional design optimization.

Figure 8:
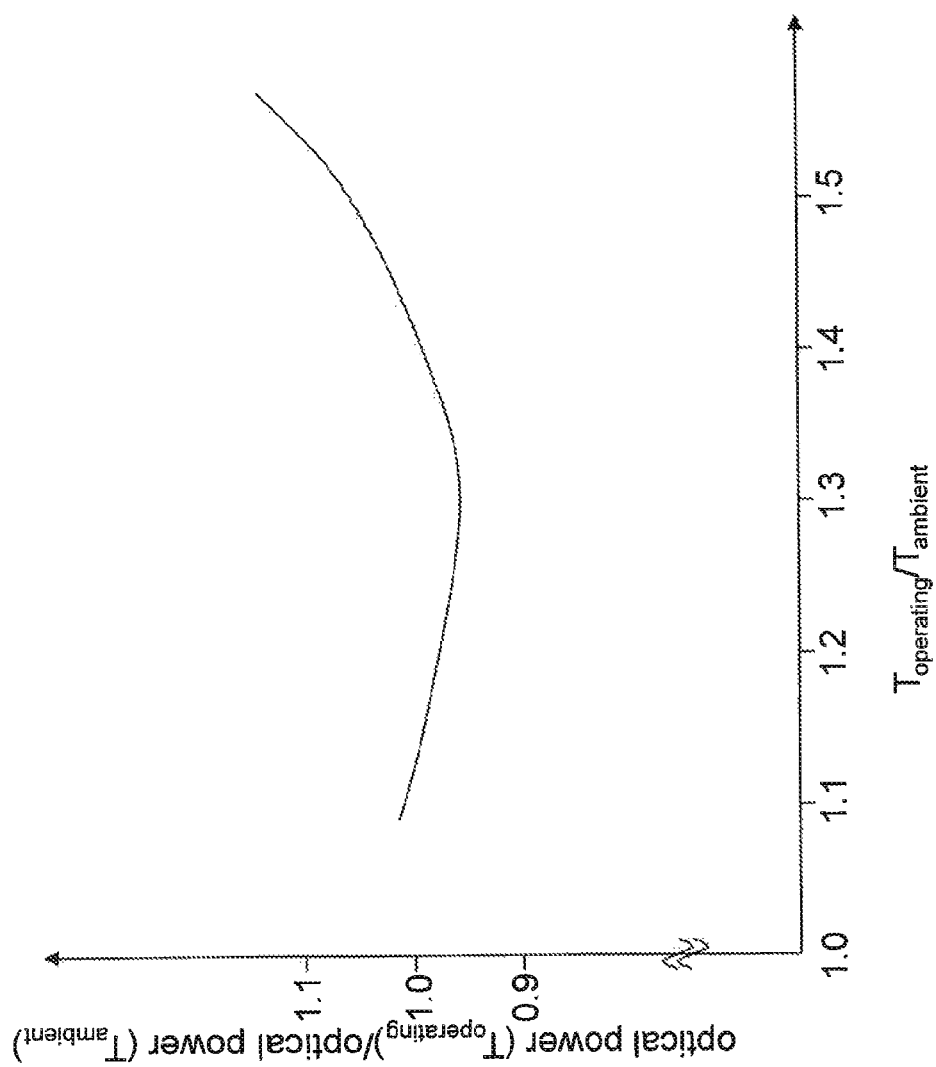
FIG. 8 illustrates the dependence of the beam optical power as a function of the operating temperature.

FIG. 8 illustrates a quantitative characterization of the suppression of thermal lensing in the laser engine 1. The horizontal axis shows the ratio of the operating temperature of the center of the crystal Toperating=Top to the ambient temperature Tambient. The vertical axis shows the optical power of the laser beam emitted by the laser engine 1. The graph shows that, even if the lasing operation heats up the laser engine 10-50% above the ambient temperature, the optical power varies only by a few %, reaching about 10% at Toperating/Tambient=150%. The optical power of the laser crystal 310 changes so little over such a wide range of operating temperatures because the refractive impact of the thermal lensing of the laser crystal 310 is minimized efficiently by the designs of FIG. 7C and FIG. 7D.

The above detailed description provides design principles and examples that can be used to achieve a functionality of changing the repetition rate without the need of making adjustments of optical elements outside the oscillator 100, including (i) using dispersion compensation inside the amplifier 300; (ii) using an integrated stretcher-compressor 200; and (iii) using cavity architectures which minimize thermal lensing, as well as other design considerations described above. Laser engines using one or more of the above design features or analogues can enable the changing of the repetition rate in repetition rate ranges within changing times, causing only limited laser beam modification.

Here the repetition rate range can be 10 kHz-2 MHz, or 50 kHz-1 MHz, or 100 kHz-500 kHz, each of these ranges offering specific functionalities.

The changing time can be the time scale of a multi-step ophthalmic surgery, such as within the range of 1-120 seconds, or 10-60 seconds or 20-50 seconds, depending on the type of surgery. Laser engines with a changing time in these ranges can support a change of the repetition rate to switch from a rate necessary for a first surgical procedure to a rate necessary for a second surgical procedure.

In other cases, such as in the embodiments described in relation to FIGS. 6A-D, the changing time can be a time scale set by the scanning speed of the laser system, e.g. a multiple of the repetition times, where the multiple can be in the range of 1-10,000, or 100-1,000. Since the repetition time is about 100 microseconds (100 μs) at 10 kHz and 1 is at 1 MHz, these "scanning-changing times", or "scanning-synchronous changing times" can be in the range of 1 μs-1 s.

A linear density of the bubbles is preserved in some implementations by changing the repetition rate in response to the change of a scanning speed so that a ratio of the scanning speed and the repetition rate remains essentially constant.

The laser beam may get modified to a limited degree by the repetition rate change. This modification can be captured in various ways, including: (i) the beam diameter changes by less than 10% or 20%; or (ii) the center of the beam moves by less than 20% or 40% of the beam diameter. Here the beam diameter can be defined in different ways, such as the diameter where the intensity of the beam falls to 50% of the intensity at the center of the beam. Other definitions can be used as well.

An example is a laser engine 1 which can emit a laser beam with a repetition rate of 100 kHz and beam diameter at the focal spot of 3 microns, where the repetition rate of the laser beam can be changed to 150 kHz by adjusting only the oscillator 100 in a changing time of 15 seconds, and in spite of this considerable change, the beam is modified only to a limited degree: the focal spot diameter changes by only 15% to 3.45 microns and its center moves relative to the optical axis only by 30% of the beam diameter, i.e. by 0.9 microns. Such a laser engine can be used to perform a cataract surgery with the 100 kHz repetition rate, have its repetition rate changed to 150 kHz in 15 seconds and be used again to perform a subsequent corneal procedure with the 150 kHz repetition rate, the entire procedure taking no more than 100 or 120 seconds, while maintaining a very good beam quality.

In another example the laser engine 1 can emit a laser beam with a repetition rate of 100 kHz and beam diameter of 4 microns. When the scanning is approaching a sharp switchback of a surgical pattern where the scanning speed slows down to half of the regular scanning speed, the repetition rate can be accordingly slowed gradually to half of its value, i.e. from 100 kHz to 50 kHz to maintain a near-constant linear density of the generated bubbles or spots. If this slowdown is performed e.g. in 10 repetition times of the 100 kHz repetition rate, then the total time of changing the repetition rate is about 100 μs.

The repetition rate can be changed in several steps or gradually, the net result being that the repetition rate is changed near synchronously with the changing of the scanning time scale of the laser beam, from 100 kHz to 50 kHz in about 100 μs. The design of the laser engine 1 makes it possible to change the repetition rate in this remarkably fast time while maintaining a high laser beam quality. In an example, the laser beam diameter can be 4 microns at 100 kHz, which changes only by 10% to 3.6 microns as the repetition rate decreases to 50 kHz, and the center of the laser beam moves away from the optical axis only by 20% of the beam diameter, i.e. by 0.8 microns.

Yet another way to express how the laser engine 1 is capable of maintaining the high beam quality while changing the repetition rate is in terms of the well-known g1-g2 stability plane. Implementations of the laser engine 1 can keep the beam parameters g1 and g2 within the hyperbolic stability region in a wide range of repetition rates, e.g. in the 10 kHz-2 MHz, or 10 kHz-500 kHz, or 50 kHz-200 kHz range.

The small number of optical elements can be a critical and distinguishing characteristic of implementations of the laser engine 1 from yet another vantage point. Femtosecond lasers in general are cutting edge devices, very sensitive to and easily misaligned by environmental impacts, usage different from the instructions, and even straightforward wear, such as self-heating effects. Therefore, the optical elements of femtosecond lasers can require fine tuning, readjustment and maintenance in regular short time intervals. Typical femtosecond lasers may contain hundred or more optical elements and the malfunction of any one of those optical elements can cause the malfunction of the entire laser.

Some typical lasers can malfunction as often as after 30-60 "cycling", i.e. switching a power of the laser engine on and off. To preempt malfunctions happening in operation, operators of some laser systems have to plan regular and costly maintenance visits, with all the attendant costs and downtimes, and can still run a high risk of in-situ malfunction with disruptive consequences.

In contrast, the embodiments of the laser engine 1 can be cycled more than 120 times by switching a power on and off without needing to readjust any optical element of the laser engine 1. For some embodiments the number of cycles can be more than 180 or even 240.

In surgical operations, to minimize problems associated with the heating and cooling of the laser crystal 310, often the laser is switched on once in the morning and switched off only in the evening, i.e. surgical lasers are often cycled once a day. In a simple estimate, if lasers are used five times a week, thus approximately 20 times a month, then 30 cycling can translate to a high chance of malfunction after 1.5 month, and 60 cycling to 3 months.

In contrast, some implementations of the laser engine 1 can be cycled more than 120 times, translating to 6 months of low probability of malfunction. Other implementations can be cycled 180 or 240 times, translating into 9 months or a full year of low probability of malfunctions. Therefore, embodiments of the laser engine 1 can be operated by a preventive maintenance schedule which poses significantly lower burden on user and service provider alike. Also, such a low frequency maintenance schedule makes possible different types of maintenance, such as replacement of entire sections of the laser system. In some cases the entire laser engine 1 can be simply replaced by a freshly maintained one on-site and the maintenance of the laser engine 1 can take place in the high tech environment of a service provider's base, instead of the lower tech environment of a surgical operator.

While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

A number of implementations of imaging-guided laser surgical techniques, apparatus and systems are disclosed. However, variations and enhancements of the described implementations, and other implementations can be made based on what is described.

The invention claimed is:

1. A method of scanning with a laser system, the method comprising:
   generating femtosecond seed pulses by an oscillator;
   stretching a duration of the seed pulses by a stretcher;
   amplifying stretched seed pulses by an amplifier into laser pulses;
   compensating a group delay dispersion of the laser pulses in the range of 5,000-20,000 $fs^2$ with a dispersion compensator between end-mirrors of the amplifier;
   outputting the laser pulses from the amplifier by an electro-optical modulator at a first repetition rate;
   compressing a duration of the laser pulses to the range of 1-1,000 fs by a compressor;
   focusing the laser pulses to a focus spot in a first target region with a scanning laser delivery system;
   scanning the focus spot with the first repetition rate in the first target region with the scanning laser delivery system;
   changing the first repetition rate to a second repetition rate with a repetition-rate controller; and
   scanning the focus spot with the second repetition rate in a second target region with the scanning laser delivery system.

2. The method of claim 1, wherein:
   the first target region is at least one of a lens region and a cataract region, and
   the second target region is a corneal region.

3. The method of claim 1, wherein:
   the first target region is a corneal region, and
   the second target region is at least one of a lens region and a cataract region.

4. The method of claim 1, wherein:
   the first repetition rate is less or equal to 100 kHz; and
   the second repetition rate is greater than 100 kHz.

5. The method of claim 4, wherein:
   the second repetition rate is 150 kHz.

6. The method of claim 1, wherein:
   the compressor and the stretcher are integrated into a stretcher-compressor.

7. The method of claim 1, wherein:
   the electro-optical modulator includes a switchable polarizer,
   configured to rotate a polarization plane of the stretched pulses in the amplifier,
   the switchable polarizer having a rise time less than 5 ns.

8. The method of claim 7, the scanning laser delivery system comprising:
   a control electronics configured to apply control signals to the switchable polarizer to cause the switchable polarizer to switch with a rise time of less than 5 ns.

9. The method of claim 1, the changing the first repetition rate to a second repetition rate comprising:
   changing a number of roundtrips of laser pulses before outputting the laser pulses from the amplifier by the electro-optical modulator.

10. The method of claim 1, the changing the first repetition rate to a second repetition rate comprising:
    changing the first repetition rate to the second repetition rate in a time in the range of 1 μsec-1 sec.

* * * * *